United States Patent
Salfeld et al.

(12) 
(10) Patent No.: US 6,509,015 B1
(45) Date of Patent: Jan. 21, 2003

(54) HUMAN ANTIBODIES THAT BIND HUMAN TNFA

(75) Inventors: Jochen G. Salfeld, North Grafton, MA (US); Deborah J. Allen, London (GB); Hendricus R. J. M. Hoogenboom, Hasselt (BE); Zehra Kaymakcalan, Westboro, MA (US); Boris Labkovsky, Framingham, MA (US); John A. Mankovich, Andover, MA (US); Brian T. McGuinness, Cambridge (GB); Andrew J. Roberts, Cambridge (GB); Paul Sakorafas, Shrewsbury, MA (US); David Schoenhaut, Clifton, NJ (US); Tristan J. Vaughan, Cambridge (GB); Michael White, Framingham, MA (US); Alison J. Wilton, Cambridge (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/540,018

(22) Filed: Mar. 31, 2000

Related U.S. Application Data

(63) Continuation of application No. 08/599,226, filed on Feb. 9, 1996, now Pat. No. 6,090,382.

(51) Int. Cl.[7] .............................................. A61K 39/395
(52) U.S. Cl. ................ 424/142.1; 424/85.2; 424/145.1; 424/800; 424/810
(58) Field of Search ........................... 424/142.1, 145.1, 424/800, 810, 85.2

(56) References Cited

U.S. PATENT DOCUMENTS

| | | | |
|---|---|---|---|
| 5,231,024 A | 7/1993 | Moeller et al. | 435/240.27 |
| 5,654,407 A | 8/1997 | Boyle et al. | 530/388.15 |
| 5,795,967 A | 8/1998 | Aggarwal et al. | 530/388.23 |
| 5,859,205 A | 1/1999 | Adair et al. | 530/387.3 |
| 5,877,293 A | 3/1999 | Adair et al. | 530/387.3 |
| 5,929,212 A | 7/1999 | Jolliffe et al. | 530/387.3 |
| 5,994,510 A | 11/1999 | Adair et al. | 530/387.3 |

FOREIGN PATENT DOCUMENTS

| | | |
|---|---|---|
| EP | 351789 | 1/1990 |
| EP | 366043 | 5/1990 |
| EP | 492448 | 7/1992 |
| EP | 186833 | 8/1992 |
| EP | 614984 | 9/1994 |
| EP | 212489 | 11/1994 |
| EP | 101681 | 12/1994 |
| EP | 659766 | 6/1995 |
| GB | 2279077 | 12/1994 |
| WO | WO 91/01078 | 2/1991 |
| WO | WO 92/11383 | 7/1992 |
| WO | WO 92/16553 | 10/1992 |
| WO | WO 93/06213 | 4/1993 |
| WO | WO 94/29347 | 12/1994 |
| WO | WO 95/23813 | 9/1995 |

OTHER PUBLICATIONS

Barbuto, J.A.M. et al. "Production of Neutralizing Antibodies to Tumor Necrosis Factor by Human Tumor–Infiltrating B Lymphocytes" *Proc. Am. Assoc. Cancer Res.* 34:487, Abstract No. 2904. (Mar. 1993).

Bendtzen, K. et al. "Auto–antibodies to IL–1α and TNFα in Normal Individuals and in Infectious and Immunoinflammatory Disorders" in *The Physiological and Pathological Effects of Cytokines* (Wiely–Liss, Inc., 1990) 447–52.

Boyle, P. et al. "A Novel Monoclonal Human IgM Autoantibody which Binds Recombinant Human and Mouse Tumor Necrosis Factor–α" *Cell. Immunol.* 152:556–68 (1993).

Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.* 152:569–81 (1993).

Chow, A.W. et al. "Effect of monoclonal antibody on human tumor necrosis factor (TNF MAb) on TNFα, IL–1β, and IL–6 levels in patients with sepsis syndrome" *Clinical Research* 42:2 299A (1994).

Cox, J.P.L. et al. "A directory of human germ–line $V_k$ segments reveals a strong bias in their usage" *Eur. J. Immunol.* 24(2):827–36 (1994).

Elliot, M.J. et al. "Treatment of rheumatoid arthritis with chimeric monoclonal antibodies to tumor necrosis factor α" *Arthritis & Rheumatism* 36(12):1681–90 (1993).

Fomsguaard, A. et al. "Auto–antibodies to Tumor Necrosis Factor α in Healthy Humans and Patients with Inflammatory Diseases and Gram–Negative Bacterial Infections" *Scand. J. Immunol.* 30:219–23 (1989).

Griffiths, A.D. et al. "Human anti–self antibodies with high specificity from phage display libraries" *The EMBO J.* 12(2):725–34 (1993).

(List continued on next page.)

*Primary Examiner*—David Saunders
(74) *Attorney, Agent, or Firm*—Lahive & Cockfield, LLP; Giulio A. DeConti, Jr., Esq.; Elizabeth A. Hanley, Esq.

(57) ABSTRACT

Human antibodies, preferably recombinant human antibodies, that specifically bind to human tumor necrosis factor α (hTNFα) are disclosed. These antibodies have high affinity for hTNFα (e.g., $K_d = 10^{-8}$ M or less), a slow off rate for hTNFα dissociation (e.g., $K_{off} = 10^{-3}$ sec$^{-1}$ or less) and neutralize hTNFα activity in vitro and in vivo. An antibody of the invention can be a full-length antibody or an antigen-binding portion thereof. The antibodies, or antibody portions, of the invention are useful for detecting hTNFα and for inhibiting hTNFα activity, e.g., in a human subject suffering from a disorder in which hTNFα activity is detrimental. Nucleic acids, vectors and host cells for expressing the recombinant human antibodies of the invention, and methods of synthesizing the recombinant human antibodies, are also encompassed by the invention.

100 Claims, 10 Drawing Sheets

OTHER PUBLICATIONS

Huse, W.D. et al. "Generation of a large combinatorial library of the immunoglobulin repertoire in phage lambda" *Science* 246:1275–81 (1989).

Lerner, R.A. et al. "Antibodies without immunization" *Science* 258:1313–14 (1992).

Leusch, H–G. et al. Failure to demonstrate TNFα–specific autoantibodies in human sera by ELISA and Western blot *J. Immunol. Methods* 139:145–47 (1991).

Lewis et al. *J. Cell. Biochem.* 18D:215 (1994).

Marks, J.D. et al. "By-passing immunization: Human antibodies from V-gene libraries displayed on phage" *J. Mol. Biol.* 222:581–97 (1991).

Möller et al. "Monoclonal antibodies to human tumors necrosis factor α: in vitro and vivo application" *Cytokine* 2(3):162–69 (1990).

Tomlinson, I.M. et al. "The repertoire of human germline $V_H$ sequences reveals about fifty groups of $V_H$ segments with different hypervariable loops" *J. Mol. Biol.* 227:776–98 (1992).

Tomlinson, I.M. et al. "The structural repertoire of the human $V_k$ domain" *The EMBO J.* 14(18):4628–38 (1995).

Tracey, K.J. et al. "Tumor necrosis factor: A pleiotropic cytokine and therapeutic target" *Annu. Rev. Med.* 45:491–503 (1994).

Winter, G. et al. "Humanized antibodies" *Immunol. Today* 14(6):243–46 (1993).

Figure 1A

|  | | | | CDR L3 | | | | | | | |
|---|---|---|---|---|---|---|---|---|---|---|---|
|  | | | | 1 | 2 | 3 | 4 | 5 | 6 | 7 | 8 | 9 | | |
| 2SD4 VL | GVPSRFSGSGSGTDFTLTISSLQPEDVATYYC | Q | K | Y | N | S | A | P | Y | A | FGQGTKVEIK |
| EP B12 | . | . | . | . | . | . | . | . | . | . | . |
| VL10E4 | . | . | . | . | . | . | R | . | . | T | . |
| VL100A9 | . | . | . | Q | R | . | . | . | . | T | A |
| VL100D2 | . | . | . | S | . | . | . | . | . | T | . |
| VL10F4 | . | . | . | . | . | . | R | . | . | T | P |
| LOE5 | . | . | . | . | . | . | . | . | . | Y | . |
| VL10F9 | . | . | . | . | . | . | R | . | . | T | S |
| VL10F10 | . | . | . | . | . | . | . | . | . | T | . |
| VL10G7 | . | . | . | . | . | . | . | . | . | N | P |
| VL10G9 | . | . | . | . | . | . | . | . | . | T | . |
| VL10H1 | . | . | . | . | T | . | . | . | . | N | . |
| VL10H10 | . | . | . | . | . | . | R | . | A | S | . |
| VL1B7 | . | . | Q | . | . | . | . | . | D | T | . |
| VL1C1 | . | . | . | . | . | . | . | . | . | T | W |
| VL1C7 | . | . | . | . | . | . | D | . | . | T | . |
| VL0.1F4 | . | . | . | . | . | . | . | . | . | T | . |
| VL0.1H8 | . | . | R | . | . | . | R | P | . | T | . |
| LOE7 | . | . | R | . | . | . | R | . | . | T | R |
| LOE7.A | . | . | R | . | . | . | R | . | . | T | . |
| LOE7.T | . | . | R | . | . | . | R | . | . | T | . |
| D2E7 VL | GVPSRFSGSGSGTDFTLTISSLQPEDVATYYC | Q | R | Y | N | R | A | P | Y | T | FGQGTKVEIK |
| LD2E7*.A1 | . | A | . | . | . | . | . | . | . | . | . |
| LD2E7*.A3 | . | . | A | . | . | . | . | . | . | . | A |
| LD2E7*.A4 | . | . | A | . | . | . | . | . | . | . | . |
| LD2E7*.A5 | . | . | A | . | . | . | . | . | . | . | . |
| LD2E7*.A7 | . | . | . | . | . | . | . | . | . | A | . |
| LD2E7*.A8 | . | . | . | . | . | . | . | . | . | A | . |

Figure 1B

| | | CDR H1 | | CDR H2 | |
|---|---|---|---|---|---|
| 2SD4 VH | QVQLVESGGGLVQPGRSLRLSCAASGFTFD | DYAMH | WVRQAPGKGLDWVS | AITWNSGHIDYADSVEG | |
| VH1B11 | . . . . . . . . . . . . . . . . . . . . . . . . . . . . . | . . . . . | . . . . . . . . . . . . . | . . . . . . . . . . . . . . . . . | |
| VH1D8 | . . . . . . . . . . . . . . . . . . . . . . . . . . . . . | . . . . . | . . . . . . . . . . . . . | . . . . . . . . . . . . . . . . . | |
| VH1A11 | . . . . . . . . . . . . . . . . . . . . . . . . . . . . . | . . . . . | . . . . . . . . . . . . . | . . . . . . . . . . . . . . . . . | |
| VH1B12 | . . . . . . . . . . . . . . . . . . . . . . . . . . . . . | . . . . . | . . . . . . . . . . . . . | . . . . . . . . . . . . . . . . . | |
| VH1-D2 | . . . . . . . . . . . . . . . . . . . . . . . . . . . . . | . . . . . | . . . . . . . . . . . . . | . . . . . . . . . . . . . . . . . | |
| VH1E4 | . . . . . . . . . . . . . . . . . . . . . . . . . . . . . | . . . . . | . . . . . . . . . . . . . | . . . . . . . . . . . . . . . . . | |
| VH1F6 | . . . . . . . . . . . . . . . . . . . . . . . . . . . . . | . . . . . | . . . . . . . . . . . . . | . . . . . . . . . . . . . . . . . | |
| VH1G1 | . . . . . . . . . . . . . . . . . . . . . . . . . . . . . | . . . . . | . . . . . . . . . . . . . | . . . . . . . . . . . . . . . . . | |
| 3C-H2 | . . . . . . . . . . . . . . . . . . . . . . . . . . . . . | . . . . . | . . . . . . . . . . . . . | . . . . . . . . . . . . . . . . . | |
| VH1-D2.N | . . . . . . . . . . . . . . . . . . . . . . . . . . . . . | . . . . . | . . . . . . . . . . . . . | . . . . . . . . . . . . . . . . . | |
| VH1-D2.Y | . . . . . . . . . . . . . . . . . . . . . . . . . . . . . | . . . . . | . . . . . . . . . . . . . | . . . . . . . . . . . . . . . . . | |
| D2E7 VH | EVQLVESGGGLVQPGRSLRLSCAASGFTFD | DYAMH | WVRQAPGKGLEWVS | AITWNSGHIDYADSVEG | |
| HD2E7*.A1 | . . . . . . . . . . . . . . . . . . . . . . . . . . . . . | . . . . . | . . . . . . . . . . . . . | . . . . . . . . . . . . . . . . . | |
| HD2E7*.A2 | . . . . . . . . . . . . . . . . . . . . . . . . . . . . . | . . . . . | . . . . . . . . . . . . . | . . . . . . . . . . . . . . . . . | |
| HD2E7*.A3 | . . . . . . . . . . . . . . . . . . . . . . . . . . . . . | . . . . . | . . . . . . . . . . . . . | . . . . . . . . . . . . . . . . . | |
| HD2E7*.A4 | . . . . . . . . . . . . . . . . . . . . . . . . . . . . . | . . . . . | . . . . . . . . . . . . . | . . . . . . . . . . . . . . . . . | |
| HD2E7*.A5 | . . . . . . . . . . . . . . . . . . . . . . . . . . . . . | . . . . . | . . . . . . . . . . . . . | . . . . . . . . . . . . . . . . . | |
| HD2E7*.A6 | . . . . . . . . . . . . . . . . . . . . . . . . . . . . . | . . . . . | . . . . . . . . . . . . . | . . . . . . . . . . . . . . . . . | |
| HD2E7*.A7 | . . . . . . . . . . . . . . . . . . . . . . . . . . . . . | . . . . . | . . . . . . . . . . . . . | . . . . . . . . . . . . . . . . . | |
| HD2E7*.A8 | . . . . . . . . . . . . . . . . . . . . . . . . . . . . . | . . . . . | . . . . . . . . . . . . . | . . . . . . . . . . . . . . . . . | |
| HD2E7*.A9 | . . . . . . . . . . . . . . . . . . . . . . . . . . . . . | . . . . . | . . . . . . . . . . . . . | . . . . . . . . . . . . . . . . . | |

```
                                                                    CDR  H3
                                                       1 2 3 4 5 6 7 8 9 10 11 12
2SD4 VH   RFAVSRDNAKNALYLQMNSLRPEDTAVYYCTK             A S Y L S T S S S L  D  N    WGQGTLVTVSS
   VH1B11 ..............................AR             . . . . . . . . . .  .  K    ...........
    VH1D8 ...............................A             . . . . . . . . . .  .  Y    ...........
   VH1A11 ...............................A             . . . . . . . . . .  D  Y    ...........
   VH1B12 ...............................A             . . . . . . F . . .  .  Y    ...........
   VH1-D2 ...............................A             . V . . . . A . . .  .  Y    ...........
    VH1E4 ...............................A             . . . . . . . . . H  .  Y    ...........
    VH1F6 ........A......................A             . . . F . . . . . .  E  Y    ...........
    VH1G1 ...............................A             . . . . . A . . . .  .  Y    ...........
    3C-H2 ...............................A             . V . . . . A . . .  .  Y    ...........
 VH1-D2.N ...............................A             . V . . . . A . . .  .  N    ...........
 VH1-D2.Y ...............................A             . V . . . . A . . .  .  Y    ...........

D2E7 VH   RFTISRDNAKNSLYLQMNSLRAEDTAVYYCAK             V S Y L S T A S S L  D  Y    WGQGTLVTVSS
 HD2E7*.A1 .............................                . A . . . . . . . .  .  .    ...........
 HD2E7*.A2 .............................                . . A . . . . . . .  .  .    ...........
 HD2E7*.A3 .............................                . . . A . . . . . .  .  .    ...........
 HD2E7*.A4 .............................                . . . . A . . . . .  .  .    ...........
 HD2E7*.A5 .............................                . . . . . A . . . .  .  .    ...........
 HD2E7*.A6 .............................                . . . . . . . A . .  .  .    ...........
 HD2E7*.A7 .............................                . . . . . . . . A .  .  .    ...........
 HD2E7*.A8 .............................                . . . . . . . . . A  .  .    ...........
 HD2E7*.A9 .............................                . . . . . . . . . .  A  .    ...........
```

```
GAC ATC CAG ATG ACC CAG TCT CCA TCC TCC CTG TCT GCA TCT GTA
 D   I   Q   M   T   Q   S   P   S   S   L   S   A   S   V
                                                    CDR L1
GGG GAC AGA GTC ACC ATC ACT TGT CGG GCA AGT CAG GGC ATC AGA
 G   D   R   V   T   I   T   C   R   A   S   Q   G   I   R

AAT TAC TTA GCC TGG TAT CAG CAA AAA CCA GGG AAA GCC CCT AAG
 N   Y   L   A   W   Y   Q   Q   K   P   G   K   A   P   K
                            CDR L2
CTC CTG ATC TAT GCT GCA TCC ACT TTG CAA TCA GGG GTC CCA TCT
 L   L   I   Y   A   A   S   T   L   Q   S   G   V   P   S

CGG TTC AGT GGC AGT GGA TCT GGG ACA GAT TTC ACT CTC ACC ATC
 R   F   S   G   S   G   S   G   T   D   F   T   L   T   I

AGC AGC CTA CAG CCT GAA GAT GTT GCA ACT TAT TAC TGT CAA AGG
 S   S   L   Q   P   E   D   V   A   T   Y   Y   C   Q   R
  CDR L3
TAT AAC CGT GCA CCG TAT ACT TTT GGC CAG GGG ACC AAG GTG GAA
 Y   N   R   A   P   Y   T   F   G   Q   G   T   K   V   E

ATC AAA
 I   K
```

| GAG | GTG | CAG | CTG | GTG | GAG | TCT | GGG | GGA | GGC | TTG | GTA | CAG | CCC | GGC |
|---|---|---|---|---|---|---|---|---|---|---|---|---|---|---|
| E | V | Q | L | V | E | S | G | G | G | L | V | Q | P | G |

| AGG | TCC | CTG | AGA | CTC | TCC | TGT | GCG | GCC | TCT | GGA | TTC | ACC | TTT | GAT |
|---|---|---|---|---|---|---|---|---|---|---|---|---|---|---|
| R | S | L | R | L | S | C | A | A | S | G | F | T | F | D |

CDR H1

| GAT | TAT | GCC | ATG | CAC | TGG | GTC | CGG | CAA | GCT | CCA | GGG | AAG | GGC | CTG |
|---|---|---|---|---|---|---|---|---|---|---|---|---|---|---|
| D | Y | A | M | H | W | V | R | Q | A | P | G | K | G | L |

CDR H2

| GAA | TGG | GTC | TCA | GCT | ATC | ACT | TGG | AAT | AGT | GGT | CAC | ATA | GAC | TAT |
|---|---|---|---|---|---|---|---|---|---|---|---|---|---|---|
| E | W | V | S | A | I | T | W | N | S | G | H | I | D | Y |

| GCG | GAC | TCT | GTG | GAG | GGC | CGA | TTC | ACC | ATC | TCC | AGA | GAC | AAC | GCC |
|---|---|---|---|---|---|---|---|---|---|---|---|---|---|---|
| A | D | S | V | E | G | R | F | T | I | S | R | D | N | A |

| AAG | AAC | TCC | CTG | TAT | CTG | CAA | ATG | AAC | AGT | CTG | AGA | GCT | GAG | GAT |
|---|---|---|---|---|---|---|---|---|---|---|---|---|---|---|
| K | N | S | L | Y | L | Q | M | N | S | L | R | A | E | D |

CDR H3

| ACG | GCC | GTA | TAT | TAC | TGT | GCG | AAA | GTC | TCG | TAC | CTT | AGC | ACC | GCG |
|---|---|---|---|---|---|---|---|---|---|---|---|---|---|---|
| T | A | V | Y | Y | C | A | K | V | S | Y | L | S | T | A |

| TCC | TCC | CTT | GAC | TAT | TGG | GGC | CAA | GGT | ACC | CTG | GTC | ACC | GTC | TCG |
|---|---|---|---|---|---|---|---|---|---|---|---|---|---|---|
| S | S | L | D | Y | W | G | Q | G | T | L | V | T | V | S |

| AGT |
|---|
| S |

FIGURE 8

HUMAN ANTIBODIES THAT BIND HUMAN TNFA

This application is a continuation application of Ser. No. 08/599,226, filed on Feb. 9, 1996, issued as U.S. Pat. No. 6,090,382. The contents of all of the aforementioned application(s) are hereby incorporated by reference.

BACKGROUND OF THE INVENTION

Tumor necrosis factor α (TNFα) is a cytokine produced by numerous cell types, including monocytes and macrophages, that was originally identified based on its capacity to induce the necrosis of certain mouse tumors (see e.g., Old, L. (1985) *Science* 230:630–632). Subsequently, a factor termed cachectin, associated with cachexia, was shown to be the same molecule as TNFα. TNFα has been implicated in mediating shock (see e.g., Beutler, B. and Cerami, A. (1988) *Annu. Rev. Biochem.* 57:505–518; Beutler, B. and Cerami, A. (1989) *Annu. Rev. Immunol.* 7:625–655). Furthermore, TNFα has been implicated in the pathophysiology of a variety of other human diseases and disorders, including sepsis, infections, autoimmune diseases, transplant rejection and graft-versus-host disease (see e.g., Vasilli, P. (1992) *Annu. Rev. Immunol.* 10:411–452; Tracey, K. J. and Cerami, A. (1994) *Annu. Rev. Med.* 45:491–503).

Because of the harmful role of human TNFα (hTNFα) in a variety of human disorders, therapeutic strategies have been designed to inhibit or counteract hTNFα activity. In particular, antibodies that bind to, and neutralize, hTNFα have been sought as a means to inhibit hTNFα activity. Some of the earliest of such antibodies were mouse monoclonal antibodies (mAbs), secreted by hybridomas prepared from lymphocytes of mice immunized with hTNFα (see e.g., Hahn T; et al., (1985) *Proc Natl Acad Sci USA* 82: 3814–3818; Liang, C-M., et al. (1986) *Biochem. Biophys. Res. Commun.* 137:847–854; Hirai, M., et al. (1987) *J. Immunol. Methods* 96:57–62; Fendly, B. M., et al. (1987) *Hybridoma* 6:359–370; Möller, A., et al. (1990) *Cytokine* 2:162–169; U.S. Pat. No. 5,231,024 to Moeller et al.; European Patent Publication No. 186 833 B1 by Wallach, D.; European Patent Application Publication No. 218 868 A1 by Old et al.; European Patent Publication No. 260 610 B1 by Moeller, A., et al.). While these mouse anti-hTNFα antibodies often displayed high affinity for hTNFα (e.g., Kd≦$10^{-9}$M) and were able to neutralize hTNFα activity, their use in vivo may be limited by problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In an attempt to overcome the problems associated with use of fully-murine antibodies in humans, murine anti-hTNFα antibodies have been genetically engineered to be more "human-like." For example, chimeric antibodies, in which the variable regions of the antibody chains are murine-derived and the constant regions of the antibody chains are human-derived, have been prepared (Knight, D. M, et al. (1993) *Mol. Immunol.* 30:1443–1453; PCT Publication No. WO 92/16553 by Daddona, P. E., et al.). Additionally, humanized antibodies, in which the hypervariable domains of the antibody variable regions are murine-derived but the remainder of the variable regions and the antibody constant regions are human-derived, have also been prepared (PCT Publication No. WO 92/11383 by Adair, J. R., et al.). However, because these chimeric and humanized antibodies still retain some murine sequences, they still may elicit an unwanted immune reaction, the human anti-chimeric antibody (HACA) reaction, especially when administered for prolonged periods, e.g., for chronic indications, such as rheumatoid arthritis (see e.g., Elliott, M. J., et al. (1994) *Lancet* 344:1125–1127; Elliot, M. J., et al. (1994) *Lancet* 344:1105–1110).

A preferred hTNFα inhibitory agent to murine mAbs or derivatives thereof (e.g., chimeric or humanized antibodies) would be an entirely human anti-hTNFα antibody, since such an agent should not elicit the HAMA reaction, even if used for prolonged periods. Human monoclonal autoantibodies against hTNFα have been prepared using human hybridoma techniques (Boyle, P., et al. (1993) *Cell. Immunol.* 152:556–568; Boyle, P., et al. (1993) *Cell. Immunol.* 152:569–581; European Patent Application Publication No. 614 984 A2 by Boyle, et al.). However, these hybridoma-derived monoclonal autoantibodies were reported to have an affinity for hTNFα that was too low to calculate by conventional methods, were unable to bind soluble hTNFα and were unable to neutralize hTNFα-induced cytotoxicity (see Boyle, et al.; supra). Moreover, the success of the human hybridoma technique depends upon the natural presence in human peripheral blood of lymphocytes producing autoantibodies specific for hTNFα. Certain studies have detected serum autoantibodies against hTNFα in human subjects (Fomsgaard, A., et al. (1989) *Scand. J. Immunol.* 30:219–223; Bendtzen, K., et al. (1990) *Prog. Leukocyte Biol.* 10B:447–452), whereas others have not (Leusch, H-G., et al. (1991) *J. Immunol. Methods* 139:145–147).

Alternative to naturally-occurring human anti-hTNFα antibodies would be a recombinant hTNFα antibody. Recombinant human antibodies that bind hTNFα with relatively low affinity (i.e., $K_d \sim 10^{-7}$M) and a fast off rate (i.e., $K_{off} \sim 10^{-2}$ $sec^{-1}$) have been described (Griffiths, A. D., et al. (1993) *EMBO J.* 12:725–734). However, because of their relatively fast dissociation kinetics, these antibodies may not be suitable for therapeutic use. Additionally, a recombinant human anti-hTNFα has been described that does not neutralize hTNFα activity, but rather enhances binding of hTNFα to the surface of cells and enhances internalization of hTNFα (Lidbury, A., et al. (1994) *Biotechnol. Ther.* 5:27–45; PCT Publication No. WO 92/03145 by Aston, R. et al.)

Accordingly, human antibodies, such as recombinant human antibodies, that bind soluble hTNFα with high affinity and slow dissociation kinetics and that have the capacity to neutralize hTNFα activity, including hTNFα-induced cytotoxicity (in vitro and in vivo) and hTNFα-induced cell activation, are still needed.

SUMMARY OF THE INVENTION

This invention provides human antibodies, preferably recombinant human antibodies, that specifically bind to human TNFα. The antibodies of the invention are characterized by binding to hTNFα with high affinity and slow dissociation kinetics and by neutralizing hTNFα activity, including hTNFα-induced cytotoxicity (in vitro and in vivo) and hTNFα-induced cellular activation. The antibodies can be full-length (e.g., an IgG1 or IgG4 antibody) or can comprise only an antigen-binding portion (e.g., a Fab, F(ab')$_2$ or scFv fragment). The most preferred recombinant antibody of the invention, termed D2E7, has a light chain CDR3 domain comprising the amino acid sequence of SEQ ID NO: 3 and a heavy chain CDR3 domain comprising the amino acid sequence of SEQ ID NO: 4. Preferably, the D2E7 antibody has a light chain variable region (LCVR) comprising the amino acid sequence of SEQ ID NO: 1 and a heavy chain variable region (HCVR) comprising the amino acid sequence of SEQ ID NO: 2.

In one embodiment, the invention provides an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1\times10^{-8}$ M or less, even more preferably with an IC$_{50}$ of $1\times10^{-9}$ M or less and still more preferably with an IC$_{50}$ of $1\times10^{-10}$ M or less.

In another embodiment, the invention provides a human antibody, or antigen-binding portion thereof, with the following characteristics:
  a) dissociates from human TNFα with a $K_{off}$ of $1\times10^{-3}$ s$^{-1}$ or less, as determined by surface plasmon resonance;
  b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;
  c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5\times10^{-4}$ s$^{-1}$ or less. Still more preferably, the antibody, or antigen-binding portion thereof, dissociates from human TNFα with a $K_{off}$ of $1\times10^{-4}$ s$^{-1}$ or less.

In yet another embodiment, the invention provides a human antibody, or an antigen-binding portion thereof, with an LCVR having CDR3 domain comprising the amino acid sequence of SEQ ID NO: 3, or modified from SEQ ID NO: 3 by a single alanine substitution at position 1, 4, 5, 7 or 8, and with an HCVR having a CDR3 domain comprising the amino acid sequence of SEQ ID NO: 4, or modified from SEQ ID NO: 4 by a single alanine substitution at position 2, 3, 4, 5, 6, 8, 9, 10 or 11. More preferably, the LCVR further has a CDR2 domain comprising the amino acid sequence of SEQ ID NO: 5 and the HCVR further has a CDR2 domain comprising the amino acid sequence of SEQ ID NO: 6. Still more preferably, the LCVR further has CDR1 domain comprising the amino acid sequence of SEQ ID NO: 7 and the HCVR has a CDR1 domain comprising the amino acid sequence of SEQ ID NO: 8.

In still another embodiment, the invention provides an isolated human antibody, or an antigen binding portion thereof, with an LCVR comprising the amino acid sequence of SEQ ID NO: 1 and an HCVR comprising the amino acid sequence of SEQ ID NO: 2. In certain embodiments, the antibody has an IgG1 heavy chain constant region or an IgG4 heavy chain constant region. In yet other embodiments, the antibody is a Fab fragment, an F(ab')$_2$ fragment or a single chain Fv fragment.

In still other embodiments, the invention provides antibodies, or antigen-binding portions thereof, with an LCVR having CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 or with an HCVR having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

In yet another embodiment, the invention provides an isolated human antibody, or antigen-binding portion thereof, that neutralizes the activity of human TNFα, chimpanzee TNFα and at least one additional primate TNFα selected from the group consisting of baboon TNFα, marmoset TNFα, cynomolgus TNFα and rhesus TNFα. In one subembodiment, the isolated human antibody, or antigen-binding portion thereof, also neutralizes the activity of mouse TNFα. In another subembodiment, the isolated human antibody, or antigen-binding portion thereof, also neutralizes the activity of pig TNFα.

Another aspect of the invention pertains to nucleic acid molecules encoding the antibodies, or antigen-binding portions, of the invention. A preferred nucleic acid of the invention, encoding a D2E7 LCVR, has the nucleotide sequence shown in FIG. 7 and SEQ ID NO: 36. Another preferred nucleic acid of the invention, encoding a D2E7 HCVR, has the nucleotide sequence shown in FIG. 8 and SEQ ID NO: 37. Recombinant expression vectors carrying the antibody-encoding nucleic acids of the invention, and host cells into which such vectors have been introduced, are also encompassed by the invention, as are methods of making the antibodies of the invention by culturing the host cells of the invention.

Yet another aspect of the invention pertains to methods for inhibiting human TNFα activity using an antibody, or antigen-binding portion thereof, of the invention. In one embodiment, the method comprises contacting human TNFα with the antibody of the invention, or antigen-binding portion thereof, such that human TNFα activity is inhibited. In another embodiment, the method comprises administering an antibody of the invention, or antigen-binding portion thereof, to a human subject suffering from a disorder in which TNFα activity is detrimental such that human TNFα activity in the human subject is inhibited. The disorder can be, for example, sepsis, an autoimmune disease (e.g., rheumatoid arthritis, allergy, multiple sclerosis, autoimmune diabetes, autoimmune uveitis and nephrotic syndrome), an infectious disease, a malignancy, transplant rejection or graft-versus-host disease, a pulmonary disorder, a bone disorder, an intestinal disorder or a cardiac disorder.

BRIEF DESCRIPTION OF THE DRAWINGS

FIGS. 1A and 1B show the amino acid sequences of the light chain variable region of D2E7 (D2E7 VL; also shown in SEQ ID NO: 1), alanine-scan mutants of D2E7 VL (LD2E7*.A1, LD2E7*.A3, LD2E7*.A4, LD2E7*.A5, LD2E7*.A7 and LD2E7*.A8), the light chain variable region of the D2E7-related antibody 2SD4 (2SD4 VL; also shown in SEQ ID NO: 9) and other D2E7-related light chain variable regions (EP B12, VL10E4, VL100A9, VL100D2, VL10F4, LOE5, VLLOF9, VLLOF10, VLLOG7, VLLOG9, VLLOH1, VLLOH10, VL1B7, VL1C1, VL1C7, VL0.1F4, VL0.1H8, LOE7, LOE7.A and LOE7.T). FIG. 1A shows the FR1, CDR1, FR2 and CDR2 domains. FIG. 1B shows the FR3, CDR3 and FR4 domains. The light chain CDR1 ("CDR L1"), CDR2 ("CDR L2") and CDR3 ("CDR L3") domains are boxed.

FIGS. 2A and 2B show the amino acid sequences of the heavy chain variable region of D2E7 (D2E7 VH; also shown in SEQ ID NO: 2), alanine-scan mutants of D2E7 VH (HD2E7*.A1, HD2E7*.A2, HD2E7*.A3, HD2E7*.A4, HD2E7*.A5, HD2E7*.A6, HD2E7*.A7, HD2E7*.A8 and HD2E7*.A9), the heavy chain variable region of the D2E7-related antibody 2SD4 (2SD4 VH; also shown in SEQ ID NO: 10) and other D2E7-related heavy chain variable regions (VH1B11, VH1D8, VH1A11, VH1B12, VH1-D2, VH1E4, VH1F6, VH1G1, 3C-H2, VH1-D2.N and VH1-D2.Y). FIG. 2A shows the FR1, CDR1, FR2 and CDR2 domains. FIG. 2B shows the FR3, CDR3 and FR4 domains. The heavy chain CDR1 ("CDR H1"), CDR2 ("CDR H2") and CDR3 ("CDR H3 ") domains are boxed.

FIG. 7 shows the nucleotide sequence of the light chain variable region of D2E7, with the predicted amino acid sequence below the nucleotide sequence. The CDR L1, CDR L2 and CDR L3 regions are underlined.

FIG. 8 shows the nucleotide sequence of the heavy chain variable region of D2E7, with the predicted amino acid sequence below the nucleotide sequence. The CDR H1, CDR H2 and CDR H3 regions are underlined.

DETAILED DESCRIPTION OF THE INVENTION

Figure 3:
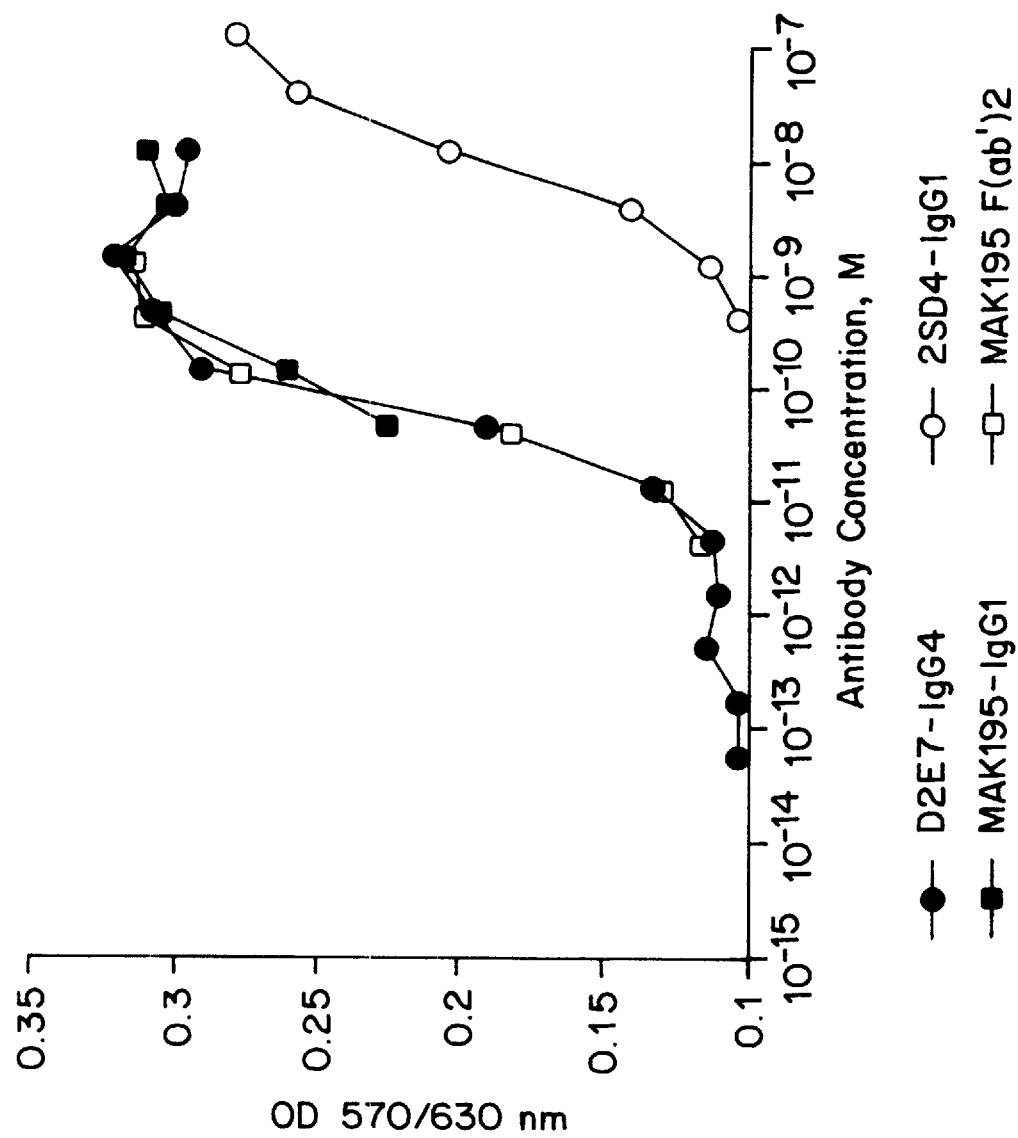
FIG. 3 is a graph depicting the inhibition of TNFα-induced L929 cytotoxicity by the human anti-hTNFα antibody D2E7, as compared to the murine anti-hTNFα antibody MAK 195 (IgG1 or Fab fragment).

This invention pertains to isolated human antibodies, or antigen-binding portions thereof, that bind to human TNFα with high affinity, a low off rate and high neutralizing capacity. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect human TNFα or to inhibit human TNFα activity, either in vitro or in vivo, are also encompassed by the invention.

In order that the present invention may be more readily understood, certain terms are first defined.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724–729; Davis, J. M., et al. (1987) *Biochemistry* 26:1322–1326; and Jones, E. Y., et al. (1989) *Nature* 338:225–228. The term human TNFα is intended to include recombinant human TNFα (rhTNFα), which can be prepared by standard recombinant expression methods or purchased commercially (R & D Systems, Catalog No. 210-TA, Minneapolis, Minn.).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain. CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 241:544–546 ), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad Sci. USA* 90:6444–6448; Poljak, R. J., et al. (1994) *Structure* 2:1121–1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93–101) and use of a cysteine residue, a marker peptide and a C-terminal polyhistidine tag to make bivalent and biotinylated scFv molecules (Kipriyanov, S. M., et al. (1994) *Mol. Immunol.* 31:1047–1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described further in Section III, below), antibodies isolated from an animal (e.g., a mouse) that is transgenic for human immunoglobulin genes (see e.g., Taylor, L. D., et al. (1992) *Nucl. Acids Res.* 20:6287–6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see Example 4). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jönsson, U., et al. (1993) *Ann. Biol. Clin.* 51:19–26; Jönsson, U., et al. (1991) *Biotechniques* 11:620–627; Johnsson, B., et al. (1995) *J. Mol. Recognit.* 8:125–131; and Johnnson, B., et al. (1991) *Anal. Biochem.* 198:268–277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-TNFα antibody contains no other sequences encoding other VH regions that bind antigens other than TNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Various aspects of the invention are described in further detail in the following subsections.

I. Human Antibodies that Bind Human TNFα

Figure 1A:
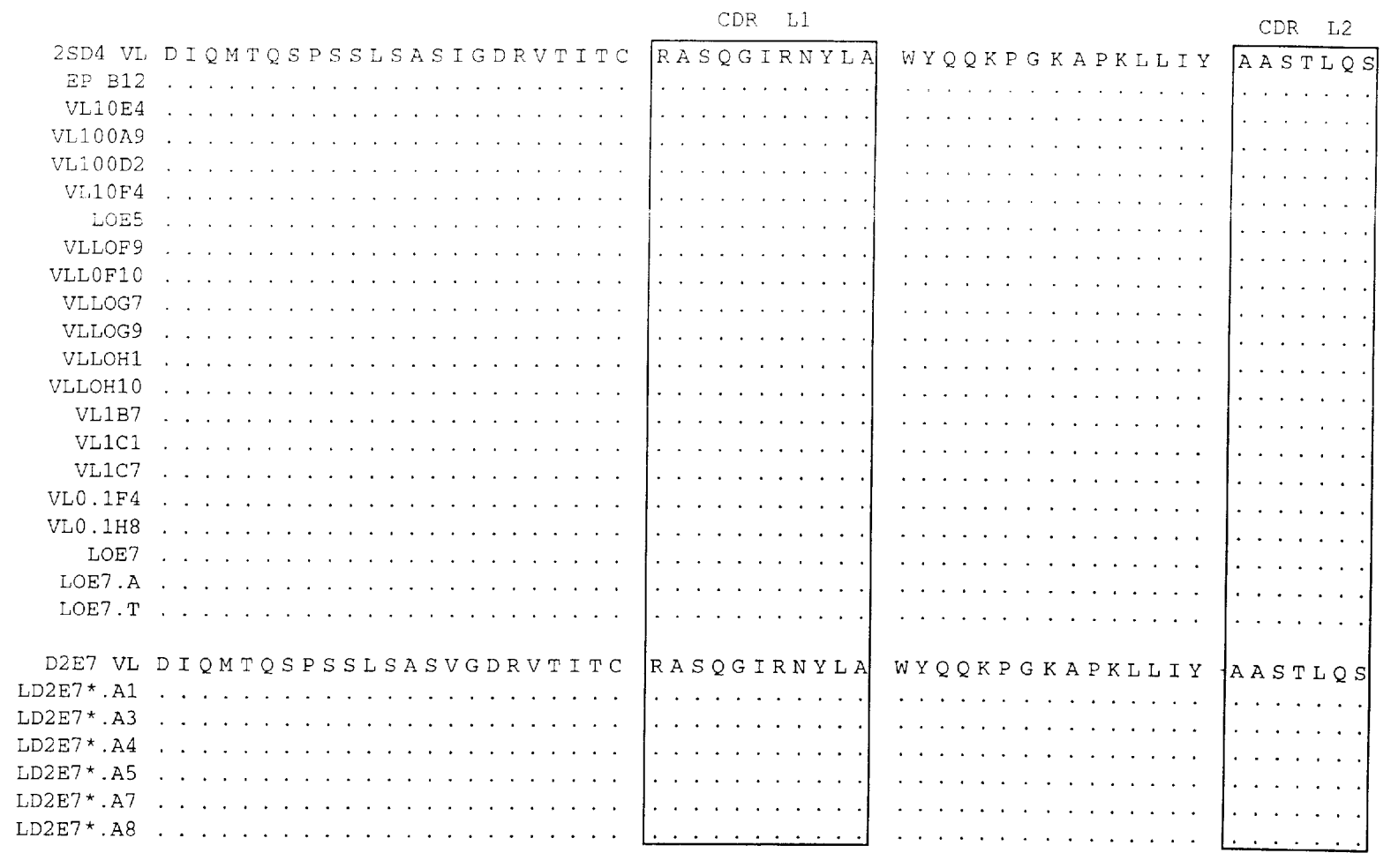

This invention provides isolated human antibodies, or antigen-binding portions thereof, that bind to human TNFα with high affinity, a low off rate and high neutralizing capacity. Preferably, the human antibodies of the invention are recombinant, neutralizing human anti-hTNFα antibodies. The most preferred recombinant, neutralizing antibody of the invention is referred to herein as D2E7 and has VL and VH sequences as shown in FIG. 1A, 1B and FIG. 2A, 2B, respectively (the amino acid sequence of the D2E7 VL region is also shown in SEQ ID NO: 1; the amino acid sequence of the D2E7 VH region is also shown in SEQ ID NO: 2). The binding properties of D2E7, as compared to the murine anti-hTNFα MAK 195 mAb that exhibits high affinity and slow dissociation kinetics and another human anti-hTNFα antibody related in sequence to D2E7, 2SD4, are summarized below:

hTNFα receptors. Furthermore, the antibody inhibits hTNFα-induced lethality in vivo in mice ($ED_{50}$=1–2.5 μg/mouse).

Regarding the binding specificity of D2E7, this antibody binds to human TNFα in various forms, including soluble hTNFα, transmembrane hTNFα and hTNFα bound to cellular receptors. D2E7 does not specifically bind to other cytokines, such as lymphotoxin (TNFβ), IL-1α, IL-1β, IL-2, IL-4, IL-6, IL-8f, IFNγ and TGFβ. However, D2E7 does exhibit crossreactivity to tumor necrosis factors from other species. For example, the antibody neutralizes the activity of at least five primate TNFαs (chimpanzee, baboon, marmoset, cynomolgus and rhesus) with approximately equivalent $IC_{50}$ values as for neutralization of hTNFα (see Example 4, subsection E). D2E7 also neutralizes the activity of mouse TNFα, although approximately 1000-fold less well than human TNFα (see Example 4, subsection E). D2E7 also binds to porcine TNFα.

In one aspect, the invention pertains to D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity. In one embodiment, the invention provides an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1\times10^{-8}$ M or less, even more preferably with an $IC_{50}$ of $1\times10^{-9}$ M or less and still more preferably with an $IC_{50}$ of $1\times10^{-10}$ M or less. In a preferred embodiment, the

| Antibody | $K_{off}$ sec$^{-1}$ | t1/2 minutes | $k_{on}$ M$^{-1}$ sec$^{-1}$ | $K_d$* M | Stoichiometry | $K_d$** M |
|---|---|---|---|---|---|---|
| D2E7 IgG4 | $9.9 \times 10^{-5}$ | 117 | $3.8 \times 10^5$ | $2.6 \times 10^{-10}$ | 1.2 | $3.4 \times 10^{-10}$ |
| 2SD4 IgG4 | $8.4 \times 10^{-5}$ | 1 | $4.2 \times 10^5$ | $2.0 \times 10^{-8}$ | 0.8 | $4.8 \times 10^{-10}$ |
| MAK 195 IgG1 | $8.2 \times 10^{-5}$ | 141 | $1.6 \times 10^5$ | $5.1 \times 10^{-10}$ | 1.2 | $1.7 \times 10^{-10}$ |
| MAK 195 F(ab')$_2$ | $8.7 \times 10^{-5}$ | 133 | $1.9 \times 10^5$ | $4.6 \times 10^{-10}$ | 1.4 | $2.2 \times 10^{-10}$ |

*$K_d = K_{off}/k_{on}$ (kinetic analysis by surface plasmon resonance as described in Example 1)
**$K_d$ = [Ab][TNFα]/[Ab:TNFα] (equilibrium analysis)

The D2E7 antibody, and related antibodies, also exhibit a strong capacity to neutralize hTNFα activity, as assessed by several in vitro and in vivo assays (see Example 4). For example, these antibodies neutralize hTNFα-induced cytotoxicity of L929 cells with $IC_{50}$ values in the range of $10^{-7}$ M to $10^{-11}$ M. D2E7, when expressed as a full-length IgG4 antibody, neutralizes hTNFα-induced cytotoxicity of L929 cells with $IC_{50}$ of $4.7\times10^{-11}$ M. Moreover, the neutralizing capacity of D2E7 is maintained when the antibody is expressed as a Fab, F(ab')$_2$ or scFv fragment. D2E7 also inhibits TNFα-induced cellular activation, as measured by hTNFα-induced ELAM-1 expression on HUVEC ($IC_{50}$=6× $10^{-11}$ M), and binding of hTNFα to hTNFα receptors on U-937 cells ($IC_{50}$=3×10$^{-10}$ M). Regarding the latter, D2E7 inhibits the binding of hTNFα to both the p60 and p80 antibody is an isolated human recombinant antibody, or an antigen-binding portion thereof. In another preferred embodiment, the antibody also neutralizes TNFα-induced cellular activation, as assessed using a standard in vitro assay for TNFα-induced ELAM-1 expression on human umbilical vein endothelial cells (HUVEC).

Surface plasmon resonance analysis for determining $K_d$ and $K_{off}$ can be performed as described in Example 1. A standard in vitro L929 assay for determining $IC_{50}$ values is described in Example 4, subsection A. A standard in vitro assay for TNFα-induced ELAM-1 expression on human umbilical vein endothelial cells (HUVEC) is described in Example 4, subsection C. Examples of recombinant human antibodies that meet, or are predicted to meet, the aforementioned kinetic and neutralization criteria include antibodies having the following [VH/VL] pairs, the sequences of which are shown in FIGS. 1A, 1B, 2A and 2B (see also Examples 2, 3 and 4 for kinetic and neutralization analyses): [D2E7 VH/D2E7 VL]; [HD2E7*.A1/D2E7 VL], [HD2E7*.A2/D2E7 VL], [HD2E7*.A3/D2E7 VL], [HD2E7*.A4/D2E7 VL], [HD2E7*.A5/D2E7 VL], [HD2E7*.A6/D2E7 VL], [HD2E7*.A7/D2E7 VL], [HD2E7*.A8/D2E7 VL], [HD2E7*.A9/D2E7 VL], [D2E7 VH/LD2E7*.A1], [D2E7 VH/LD2E7*.A4], [D2E7 VH/LD2E7*.A5], [D2E7 VH/LD2E7*.A7], [D2E7 VH/LD2E7*.A8], [HD2E7*.A9/LD2E7*.A1], [VH1-D2/LOE7], [VH1-D2.N/LOE7.T], [VH1-D2.Y/LOE7.A], [VH1-D2.N/LOE7.A], [VH1-D2/EP B12] and [3C-H2/LOE7].

It is well known in the art that antibody heavy and light chain CDR3 domains play an important role in the binding specificity/affinity of an antibody for an antigen. Accordingly, in another aspect, the invention pertains to human antibodies that have slow dissociation kinetics for association with hTNFα and that have light and heavy chain CDR3 domains that structurally are identical to or related to those of D2E7. As demonstrated in Example 3, position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. As shown in Example 3, positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above).

Accordingly, in another embodiment, the invention provides an isolated human antibody, or antigen-binding portion thereof, with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9,10, 11 and/or 12.

More preferably, the antibody, or antigen-binding portion thereof, dissociates from human TNFα with a $K_{off}$ of $5\times10^{-4}$ s$^{-1}$ or less. Even more preferably, the antibody, or antigen-binding portion thereof, dissociates from human TNFα with a $K_{off}$ of $1\times10^{-4}$ s$^{-1}$ or less.

In yet another embodiment, the invention provides an isolated human antibody, or an antigen-binding portion thereof, with a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (ie., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_K$I human germline family, more preferably from the A20 human germline Vk gene and most preferably from the D2E7 VL framework sequences shown in FIGS. 1A and 1B. The framework regions for VH preferably are from the $V_H$3 human germline family, more preferably from the DP-31 human germline VH gene and most preferably from the D2E7 VH framework sequences shown in FIGS. 2A and 2B.

In still another embodiment, the invention provides an isolated human antibody, or an antigen binding portion thereof, with a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention provides an isolated human antibody, or an antigen-binding portions thereof, having D2E7-related VL and VH CDR3 domains, for example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

In yet another embodiment, the invention provides a human antibody, or antigen-binding portion thereof, that neutralizes the activity of human TNFα, chimpanzee TNFα and at least one additional primate TNFα selected from the group consisting of baboon TNFα, marmoset TNFα, cynomolgus TNFα and rhesus TNFα. Preferably, the antibody, or antigen-binding portion thereof, neutralizes the human, chimpanzee and/or additional primate TNFα in a standard in vitro L929 assay with an $IC_{50}$ of $1\times10^{-8}$ M or less, more preferably $1\times10^{-9}$ M or less, even more preferably $1\times10^{-10}$ M or less and still more preferably $1\times10^{-11}$ M or less. In one subembodiment, the antibody also neutralizes the activity of mouse TNFα, preferably in a standard in vitro L929 assay with an $IC_{50}$ of $1\times10^{-6}$ M or less, more preferably $1\times10^{-7}$ M or less and even more preferably $1\times10^{-8}$ M or less. In another subembodiment, the antibody also neutralizes the activity of pig TNFα, preferably with an $IC_{50}$ of $1\times10^{-6}$ M or less, more preferably $1\times10^{-7}$ M or less and even more preferably $1\times10^{-8}$ M or less. In another preferred subembodiment, the antibody is a recombinant antibody.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

II. Expression of Antibodies

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express D2E7 or a D2E7-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776–798; and Cox, J. P. L. et al. (1994) "A Directory of Human Germ-line $V_\kappa$ Segments Reveals a Strong Bias in their Usage" *Eur. J. Immunol.* 24:827–836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7- related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding D2E7 or D2E7-related VH and VL segments are obtained (by amplification and mutagenesis of germline VH and VL genes, as described above), these DNA fragments can be. further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. d(1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423–426; Huston et al. (1988) *Proc. Natl. Acad. Sci. USA* 85:5879–5883; McCafferty et al., *Nature* (1990) 348:552–554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12–13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad Sci. USA* 77:4216–4220, used with a DHFR selectable marker, e.g., as described in R. J. Kaufman and P. A. Sharp (1982) *Mol. Biol.* 159:601–621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, another aspect of the invention pertains to nucleic acid, vector and host cell compositions that can be used for recombinant expression of the antibodies and antibody portions of the invention. The nucleotide sequence encoding the D2E7 light chain variable region is shown in FIG. 7 and SEQ ID NO: 36. The CDR1 domain of the LCVR encompasses nucleotides 70–102, the CDR2 domain encompasses nucleotides 148–168 and the CDR3 domain encompasses nucleotides 265–291. The nucleotide sequence encoding the D2E7 heavy chain variable region is shown in FIG. 8 and SEQ ID NO: 37. The CDR1 domain of the HCVR encompasses nucleotides 91–105, the CDR2 domain encompasses nucleotides 148–198 and the CDR3 domain encompasses nucleotides 295–330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

In one embodiment, the invention provides an isolated nucleic acid encoding a light chain CDR3 domain comprising the amino acid sequence of SEQ ID NO: 3 (i.e., the D2E7 VL CDR3), or modified from SEQ ID NO: 3 by a single alanine substitution at position 1, 4, 5, 7 or 8 or by one to five conservative amino acid substitutions at positions 1, 3, 4, 6, 7, 8 and/or 9. This nucleic acid can encode only the CDR3 region or, more preferably, encodes an entire antibody light chain variable region (LCVR). For example, the nucleic acid can encode an LCVR having a CDR2 domain comprising the amino acid sequence of SEQ ID NO: 5 (i.e., the D2E7 VL CDR2) and a CDR1 domain comprising the amino acid sequence of SEQ ID NO: 7 (i.e., the D2E7 VL CDR1).

In another embodiment, the invention provides an isolated nucleic acid encoding a heavy chain CDR3 domain comprising the amino acid sequence of SEQ ID NO: 4 (i.e., the D2E7 VH CDR3), or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. This nucleic acid can encode only the CDR3 region or, more preferably, encodes an entire antibody heavy chain variable region (HCVR). For example, the nucleic acid can encode a HCVR having a CDR2 domain comprising the amino acid sequence of SEQ ID NO: 6 (i.e., the D2E7 VH CDR2) and a CDR1 domain comprising the amino acid sequence of SEQ ID NO: 8 (i.e., the D2E7 VH CDR1).

In yet another embodiment, the invention provides isolated nucleic acids encoding a D2E7-related CDR3 domain, e.g., comprising an amino acid sequence selected from the group consisting of: SEQ ID NO: 3, SEQ ID NO: 4, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

In still another embodiment, the invention provides an isolated nucleic acid encoding an antibody light chain variable region comprising the amino acid sequence of SEQ ID NO: 1 (i.e., the D2E7 LCVR). Preferably this nucleic acid comprises the nucleotide sequence of SEQ ID NO: 36, although the skilled artisan will appreciate that due to the degeneracy of the genetic code, other nucleotide sequences can encode the amino acid sequence of SEQ ID NO: 1. The nucleic acid can encode only the LCVR or can also encode an antibody light chain constant region, operatively linked to the LCVR. In one embodiment, this nucleic acid is in a recombinant expression vector.

In still another embodiment, the invention provides an isolated nucleic acid encoding an antibody heavy chain variable region comprising the amino acid sequence of SEQ ID NO: 2 (i.e., the D2E7 HCVR). Preferably this nucleic acid comprises the nucleotide sequence of SEQ ID NO: 37, although the skilled artisan will appreciate that due to the degeneracy of the genetic code, other nucleotide sequences can encode the amino acid sequence of SEQ ID NO: 2. The nucleic acid can encode only the HCVR or can also encode a heavy chain constant region, operatively linked to the HCVR. For example, the nucleic acid can comprise an IgG1 or IgG4 constant region. In one embodiment, this nucleic acid is in a recombinant expression vector.

The invention also provides recombinant expression vectors encoding both an antibody heavy chain and an antibody light chain. For example, in one embodiment, the invention provides a recombinant expression vector encoding:
  a) an antibody light chain having a variable region comprising the amino acid sequence of SEQ ID NO: 1 (i.e., the D2E7 LCVR); and
  b) an antibody heavy chain having a variable region comprising the amino acid sequence of SEQ ID NO: 2 (i.e., the D2E7 HCVR).

The invention also provides host cells into which one or more of the recombinant expression vectors of the invention have been introduced. Preferably, the host cell is a mammalian host cell, more preferably the host cell is a CHO cell, an NS0 cell or a COS cell. Still further the invention provides a method of synthesizing a recombinant human antibody of the invention by culturing a host cell of the invention in a suitable culture medium until a recombinant human antibody of the invention is synthesized. The method can further comprise isolating the recombinant human antibody from the culture medium.

III. Selection of Recombinant Human Antibodies

Recombinant human antibodies of the invention in addition to the D2E7 or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370–1372; Hay et al. (1992) *Hum Antibod Hybridomas* 3:81–85; Huse et al. (1989) *Science* 246:1275–1281; McCafferty et al., *Nature* (1990) 348:552–554; Griffiths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552–554; and Griffiths et al., (1993) *EMBO J* 12:725–734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section II above.

IV. Pharmaceutical Compositions and Pharmaceutical Administration

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example. liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets,.or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents. For example, an anti-hTNFα antibody or antibody portion of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. The use of the antibodies, or antibody portions, of the invention in combination with other therapeutic agents is discussed further in subsection IV.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1–20 mg/kg, more preferably 1–10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IV. Uses of the Antibodies of the Invention

Given their ability to bind to hTNFα, the anti-hTNFα antibodies, or portions thereof, of the invention can be used to detect hTNFα (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting hTNFα in a biological sample comprising contacting a biological sample with an antibody, or antibody portion, of the invention and detecting either the antibody (or antibody portion) bound to hTNFα or unbound antibody (or antibody portion), to thereby detect hTNFα in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Alternative to labeling the antibody, hTNFα can be assayed in biological fluids by a competition immunoassay utilizing rhTNFα standards labeled with a detectable substance and an unlabeled anti-hTNFα antibody. In this assay, the biological sample, the labeled rhTNFα standards and the anti-hTNFα antibody are combined and the amount of labeled rhTNFα standard bound to the unlabeled antibody is determined. The amount of hTNFα in the biological sample is inversely proportional to the amount of labeled rhTNFα standard bound to the anti-hTNFα antibody.

A D2E7 antibody of the invention can also be used to detect TNFαs from species other than humans, in particular TNFαs from primates (e.g., chimpanzee, baboon, marmoset, cynomolgus and rhesus), pig and mouse, since D2E7 can bind to each of these TNFαs (discussed further in Example 4, subsection E).

The antibodies and antibody portions of the invention are capable of neutralizing hTNFα activity both in vitro and in vivo (see Example 4). Moreover, at least some of the antibodies of the invention, such as D2E7, can neutralize TNFα activity from other species. Accordingly, the antibodies and antibody portions of the invention can be used to inhibit TNFα activity, e.g., in a cell culture containing hTNFα, in human subjects or in other mammalian subjects having TNFα with which an antibody of the invention cross-reacts (e.g. chimpanzee, baboon, marmoset, cynomolgus and rhesus, pig or mouse). In one embodiment, the invention provides a method for inhibiting TNFα activity comprising contacting TNFα with an antibody or antibody portion of the invention such that TNFα activity is inhibited. Preferably, the TNFα is human TNFα. For example, in a cell culture containing, or suspected of containing hTNFα, an antibody or antibody portion of the invention can be added to the culture medium to inhibit hTNFα activity in the culture.

In another embodiment, the invention provides a method for inhibiting TNFα activity in a subject suffering from a disorder in which TNFα activity is detrimental, comprising administering to the subject an antibody or antibody portion of the invention such that TNFα activity in the subject is inhibited. Preferably, the TNFα is human TNFα and the subject is a human subject. Alternatively, the subject can be a mammal expressing a TNFα with which an antibody of the invention cross-reacts. Still further the subject can be a mammal into which has been introduced hTNFα (e.g., by administration of hTNFα or by expression of an hTNFα transgene). An antibody of the invention can be administered to a human subject for therapeutic purposes (discussed further below). Moreover, an antibody of the invention can be administered to a non-human mammal expressing a TNFα with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of the antibodies and antibody portions of the invention in the treatment of specific disorders is discussed further below:

A. Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Tracey, K. J. and Cerami, A. (1994) Annu. Rev. Med. 45:491–503; Russell, D and Thompson, R. C. (1993) Curr. Opin. Biotech. 4:714–721). Accordingly, the human antibodies, and antibody portions, of the invention can be used to treat sepsis in any of its clinical settings, including septic shock, endotoxic shock, gram negative sepsis and toxic shock syndrome.

Furthermore, to treat sepsis, an anti-hTNFα antibody, or antibody portion, of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510).

Additionally, in a preferred embodiment, an anti-TNFα antibody or antibody portion of the invention is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L., et al.).

B. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Tracey and Cerami, supra; Arend, W. P. and Dayer, J-M. (1995) Arth. Rheum. 38:151–160; Fava, R. A., et al. (1993) Clin. Exp. Immunol. 94:261–266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) Lancet 344:1125–1127; Elliot, M. J., et al. (1994) Lancet 344:1105–1110; Rankin, E. C., et al. (1995) Br. J. Rheumatol. 34:334–342).

The human antibodies, and antibody portions of the invention can be used to treat autoimmune diseases, in particular those associated with inflammation, including rheumatoid arthritis, rheumatoid spondylitis, osteoarthritis and gouty arthritis, allergy, multiple sclerosis, autoimmune diabetes, autoimmune uveitis and nephrotic syndrome. Typically, the antibody, or antibody portion, is administered systemically, although for certain disorders, local administration of the antibody or antibody portion at a site of inflammation may be beneficial (e.g., local administration in the joints in rheumatoid arthritis or topical application to diabetic ulcers, alone or in combination with a cyclohexane-ylidene derivative as described in PCT Publication No. WO 93/19751).

C. Infectious Diseases

Tumor necrosis factor has been implicated in mediating biological effects observed in a variety of infectious diseases. For example, TNFα has been implicated in mediating brain inflammation and capillary thrombosis and infarction in malaria (see e.g., Tracey and Cerami, supra). TNFα also has been implicated in mediating brain inflammation, inducing breakdown of the blood-brain barrier, triggering septic shock syndrome and activating venous infarction in meningitis (see e.g., Tracey and Cerami, supra). TNFα also has been implicated in inducing cachexia, stimulating viral proliferation and mediating central nervous system injury in acquired immune deficiency syndrome (AIDS) (see e.g., Tracey and Cerami, supra). Accordingly, the antibodies, and antibody portions, of the invention, can be used in the treatment of infectious diseases, including bacterial meningitis (see e.g., European Pat. Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze, E., et al. (1994) Transplantation 58:675–680). The antibodies, and antibody portions, of the invention, also can be used to alleviate symptoms associated with infectious diseases, including fever and myalgias due to infection (such as influenza) and cachexia secondary to infection (e.g., secondary to AIDS or ARC).

D. Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Tracey and Cerami, supra; Eason, J. D., et al. (1995) Transplantation 59:300–305; Suthanthiran, M. and Strom, T. B. (1994) New Engl. J. Med. 331:365–375). Accordingly, the antibodies, and antibody portions, of the invention, can be used to inhibit transplant rejection, including rejections of allografts and xenografts and to inhibit GVHD. Although the antibody or antibody portion may be used alone, more preferably it is used in combination with one or more other agents that inhibit the immune response against the allograft or inhibit GVHD. For example, in one embodiment, an antibody or antibody portion of the invention is used in combination with OKT3 to inhibit OKT3-induced reactions. In another embodiment, an antibody or antibody portion of the invention is used in combination with one or more antibodies directed at other targets involved in regulating immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, an antibody or antibody portion of the invention is used in combination with one or more general immunosuppressive agents, such as cyclosporin A or FK506.

E. Malignancy

Tumor necrosis factor has been implicated in inducing cachexia, stimulating tumor growth, enhancing metastatic potential and mediating cytotoxicity in malignancies (see e.g., Tracey and Cerami, supra). Accordingly, the antibodies, and antibody portions, of the invention, can be used in the treatment of malignancies, to inhibit tumor growth or metastasis and/or to alleviate cachexia secondary to malignancy. The antibody, or antibody portion, may be administered systemically or locally to the tumor site.

F. Pulmonary Disorders

Tumor necrosis factor has been implicated in the pathophysiology of adult respiratory distress syndrome, including stimulating leukocyte-endothelial activation, directing cytotoxicity to pneumocytes and inducing vascular leakage syndrome (see e.g., Tracey and Cerami, supra). Accordingly, the antibodies, and antibody portions, of the invention, can be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis and silicosis. The antibody, or antibody portion, may be administered systemically or locally to the lung surface, for example as an aerosol.

G. Intestinal Disorders

Tumor necrosis factor has been implicated in the pathophysiology of inflammatory bowel disorders (see e.g., Tracey, K. J., et al. (1986) *Science* 234:470–474; Sun, X-M., et al. (1988) *J. Clin. Invest.* 81:1328–133 1; MacDonald, T. T., et al. (1990) *Clin. Exp. Immunol.* 81:301–305). Chimeric murine anti-hTNFα antibodies have undergone clinical testing for treatment of Crohn's disease (van Dullemen, H. M., et al. (1995) *Gastroenterology* 109:129–135). The human antibodies, and antibody portions, of the invention, also can be used to treat intestinal disorders, such as idiopathic inflammatory bowel disease, which includes two syndromes, Crohn's disease and ulcerative colitis.

H. Cardiac Disorders

The antibodies, and antibody portions, of the invention, also can be used to treat various cardiac disorders, including ischemia of the heart (see e.g., European Patent Application Publication No. EP 453 898) and heart insufficiency (weakness of the heart muscle)(see e.g., PCT Publication No. WO 94/20139).

I. Others

The antibodies, and antibody portions, of the invention, also can be used to treat various other disorders in which TNFα activity is detrimental. Examples of other diseases and disorders in which TNFα activity has been implicated in the pathophysiology, and thus which can be treated using an antibody, or antibody portion, of the invention, include inflammatory bone disorders and bone resorption disease (see e.g., Bertolini, D. R., et al. (1986) *Nature* 319:516–518; Konig, A., et al. (1988) *J. Bone Miner. Res.* 3:621–627; Lerner, U. H. and Ohlin, A. (1993) *J. Bone Miner. Res.* 8:147–155; and Shankar, G. and Stem, P. H. (1993) *Bone* 14:871–876), hepatitis, including alcoholic hepatitis (see e.g., McClain, C. J. and Cohen, D. A. (1989) *Hepatology* 9:349–351; Felver, M. E., et al. (1990) *Alcohol. Clin. Exp. Res.* 14:255–259; and Hansen, J., et al. (1994) *Hepatology* 20:461–474) and viral hepatitis (Sheron, N., et al. (1991) *J. Hepatol.* 12:241–245; and Hussain, M. J., et al. (1994) *J. Clin. Pathol.* 47:1112–1115), coagulation disturbances (see e.g., van der Poll, T., et al. (1990) *N. Engl. J. Med.* 322:1622–1627; and van der Poll, T., et al. (1991) *Prog. Clin. Biol. Res.* 367:55–60), burns (see e.g., Giroir, B. P., et al. (1994) *Am. J. Physiol.* 267:H118–124; and Liu, X. S., et al. (1994) *Burns* 20:40–44), reperfusion injury (see e.g., Scales, W. E., et al. (1994) *Am. J. Physiol.* 267:G1122–1127; Serrick, C., et al. (1994) *Transplantation* 58:1158–1162; and Yao, Y. M., et al. (1995) *Resuscitation* 29:157–168), keloid formation (see e.g., McCauley, R. L., et al. (1992) *J. Clin. Immunol.* 12:300–308), scar tissue formation and pyrexia.

This invention is further illustrated by the following examples which should not be construed as limiting. The contents of all references, patents and published patent applications cited throughout this application are hereby incorporated by reference.

EXAMPLE 1

Kinetic Analysis of Binding of Human Antibodies to hTNFα

Real-time binding interactions between ligand (biotinylated recombinant human TNFα (rhTNFα) immobilized on a biosensor matrix) and analyte (antibodies in solution) were measured by surface plasmon resonance (SPR) using the BIAcore system (Pharmacia Biosensor, Piscataway, N.J.). The system utilizes the optical properties of SPR to detect alterations in protein concentrations within a dextran biosensor matrix. Proteins are covalently bound to the dextran matrix at known concentrations. Antibodies are injected through the dextran matrix and specific binding between injected antibodies and immobilized ligand results in an increased matrix protein concentration and resultant change in the SPR signal. These changes in SPR signal are recorded as resonance units (RU) and are displayed with respect to time along the y-axis of a sensorgram.

To facilitate immobilization of biotinylated rhTNFα on the biosensor matrix, streptavidin is covalently linked via free amine groups to the dextran matrix by first activating carboxyl groups on the matrix with 100 mM N-hydroxysuccinimide (NHS) and 400 mM N-ethyl-N'-(3-diethylaminopropyl) carbodiimide hydrochloride (EDC). Next, streptavidin is injected across the activated matrix. Thirty-five microliters of streptavidin (25 μg/ml), diluted in sodium acetate, pH 4.5, is injected across the activated biosensor and free amines on the protein are bound directly to the activated carboxyl groups. Unreacted matrix EDC-esters are deactivated by an injection of 1 M ethanolamine. Streptavidin-coupled biosensor chips also are commercially available (Pharmacia BR-1000-16, Pharmacia Biosensor, Piscataway, N.J.).

Biotinylated rhTNFα was prepared by first dissolving 5.0 mg of biotin (D-biotinyl-ε-aminocaproic acid N-hydroxysuccinimide ester; Boehringer Mannheim Cat. No. 1008 960) in 500 μl dimethylsulfoxide to make a 10 mg/ml solution. Ten microliters of biotin was added per ml of rhTNFα (at 2.65 mg/ml) for a 2:1 molar ratio of biotin to rhTNFα. The reaction was mixed gently and incubated for two hours at room temperature in the dark. A PD-10 column, Sephadex G-25M (Pharmacia Catalog No. 17-0851-01) was equilibrated with 25 ml of cold PBS and loaded with 2 ml of rhTNFα-biotin per column. The column was eluted with 10×1 ml cold PBS. Fractions were collected and read at OD280 (1.0 OD=1.25 mg/ml). The appropriate fractions were pooled and stored at −80° C. until use. Biotinylated rhTNFα also is commercially available (R & D Systems Catalog No. FTA00, Minneapolis, Minn.).

Biotinylated rhTNFα to be immobilized on the matrix via streptavidin was diluted in PBS running buffer (Gibco Cat. No. 14190-144, Gibco BRL, Grand Island, N.Y.) supplemented with 0.05% (BIAcore) surfactant P20 (Pharmacia BR-1000-54, Pharmacia Biosensor, Piscataway, N.J.). To determine the capacity of rhTNFα-specific antibodies to bind immobilized rhTNFα, a binding assay was conducted as follows. Aliquots of biotinylated rhTNFα (25 nM; 10 μl aliquots) were injected through the streptavidin-coupled dextran matrix at a flow rate of 5 μl/min. Before injection of the protein and immediately afterward, PBS buffer alone flowed through each flow cell. The net difference in signal between baseline and approximately 30 sec. after completion of biotinylated rhTNFα injection was taken to represent the binding value (approximately 500 RU). Direct rhTNFα-specific antibody binding to immobilized biotinylated rhTNFα a was measured. Antibodies (20 μg/ml) were diluted in PBS running buffer and 25 μl aliquots were injected through the immobilized protein matrices at a flow rate of 5 μl/min. Prior to injection of antibody, and immediately afterwards, PBS buffer alone flowed through each flow cell. The net difference in baseline signal and signal after completion of antibody injection was taken to represent the binding value of the particular sample. Biosensor matrices were regenerated using 100 mM HCl before injection of the next sample. To determine the off rate ($K_{off}$), on rate ($K_{on}$), association rate ($K_a$) and dissociation rate ($K_d$) constants, BIAcore kinetic evaluation software (version 2.1) was used.

Representative results of D2E7 (full-length antibody) binding to biotinylated rhTNFα, as compared to the mouse mAb MAK 195 (F(ab')$_2$ fragment), are shown below in Table 1.

TABLE 1

Binding of D2E7 or MAK 195 to Biotinylated rhTNFα

| Antibody | [Ab], nM | rhTNFα, bound, RUs | Ab, bound, RUs | rhTNFα/Ab | $K_{off}$, sec$^{-1}$, (Avg) |
|---|---|---|---|---|---|
| D2E7 | 267 | 373 | 1215 | 1.14 | 8.45 × 10$^{-5}$ |
| | 133 | 420 | 1569 | 1.30 | 5.42 × 10$^{-5}$ |
| | 67 | 434 | 1633 | 1.31 | 4.75 × 10$^{-5}$ |
| | 33 | 450 | 1532 | 1.19 | 4.46 × 10$^{-5}$ |
| | 17 | 460 | 1296 | 0.98 | 3.47 × 10$^{-5}$ |
| | 8 | 486 | 936 | 0.67 | 2.63 × 10$^{-5}$ |
| | 4 | 489 | 536 | 0.38 | 2.17 × 10$^{-5}$ |
| | 2 | 470 | 244 | 0.18 | 3.68 × 10$^{-5}$ |
| | | | | | (4.38 × 10$^{-5}$) |
| MAK 195 | 400 | 375 | 881 | 1.20 | 5.38 × 10$^{-5}$ |
| | 200 | 400 | 1080 | 1.38 | 4.54 × 10$^{-5}$ |
| | 100 | 419 | 1141 | 1.39 | 3.54 × 10$^{-5}$ |
| | 50 | 427 | 1106 | 1.32 | 3.67 × 10$^{-5}$ |
| | 25 | 446 | 957 | 1.09 | 4.41 × 10$^{-5}$ |
| | 13 | 464 | 708 | 0.78 | 3.66 × 10$^{-5}$ |
| | 6 | 474 | 433 | 0.47 | 7.37 × 10$^{-5}$ |
| | 3 | 451 | 231 | 0.26 | 6.95 × 10$^{-5}$ |
| | | | | | (4.94 × 10$^{-5}$) |

EXAMPLE 2

Alanine Scanning Mutagenesis of D2E7 CDR3 Domains

A series of single alanine mutations were introduced by standard methods along the CDR3 domain of the D2E7 VL and the D2E7 VH regions. The light chain mutations are illustrated in FIG. 1B (LD2E7*.A1, LD2E7*.A3, LD2E7*.A4, LD2E7*.A5, LD2E7*.A7 and LD2E7*.A8, having an alanine mutation at position 1, 3, 4, 5, 7 or 8, respectively, of the D2E7 VL CDR3 domain). The heavy chain mutations are illustrated in FIG. 2B HD2E7*.A1, HD2E7*.A2, HD2E7*.A3, HD2E7*.A4, HD2E7*.A5, HD2E7*.A6, HD2E7*.A7, HD2E7*.A8 and HD2E7*.A9, having an alanine mutation at position 2, 3, 4, 5, 6, 7, 8, 9, 10 or 11, respectively, of the D2E7 VH CDR3 domain). The kinetics of rhTNFα interaction with an antibody composed of wild-type D2E7 VL and VH was compared to that of antibodies composed of 1) a wild-type D2E7 VL paired with an alanine-substituted D2E7 VH;2) a wild-type D2E7 VH paired with an alanine-substituted D2E7 VL; or 3) an alanine-substituted D2E7 VL paired with an alanine-substituted D2E7 VH. All antibodies were tested as full-length, IgG4 molecules.

Kinetics of interaction of antibodies with rhTNFα was determined by surface plasmon resonance as described in Example 1. The $K_{off}$ rates for the different VH/VL pairs are summarized below in Table 2:

TABLE 2

Binding of D2E7 Alanine-Scan Mutants to Biotinylated rhTNFα

| VH | VL | $K_{off}$ (sec$^{-1}$) |
|---|---|---|
| D2E7 VH | D2E7 VL | 9.65 × 10$^{-5}$ |
| HD2E7*.A1 | D2E7 VL | 1.4 × 10$^{-4}$ |
| HD2E7*.A2 | D2E7 VL | 4.6 × 10$^{-4}$ |
| HD2E7*.A3 | D2E7 VL | 8.15 × 10$^{-4}$ |
| HD2E7*.A4 | D2E7 VL | 1.8 × 10$^{-4}$ |
| HD2E7*.A5 | D2E7 VL | 2.35 × 10$^{-4}$ |
| HD2E7*.A6 | D2E7 VL | 2.9 × 10$^{-4}$ |
| HD2E7*.A7 | D2E7 VL | 1.0 × 10$^{-4}$ |
| HD2E7*.A8 | D2E7 VL | 3.1 × 10$^{-4}$ |
| HD2E7*.A9 | D2E7 VL | 8.1 × 10$^{-4}$ |
| D2E7 VH | LD2E7*.A1 | 6.6 × 10$^{-5}$ |
| D2E7 VH | LD2E7*.A3 | NOT DETECTABLE |
| D2E7 VH | LD2E7*.A4 | 1.75 × 10$^{-4}$ |
| D2E7 VH | LD2E7*.A5 | 1.8 × 10$^{-4}$ |
| D2E7 VH | LD2E7*.A7 | 1.4 × 10$^{-4}$ |
| D2E7 VH | LD2E7*.A8 | 3.65 × 10$^{-4}$ |
| HD2E7*.A9 | LD2E7*.A1 | 1.05 × 10$^{-4}$ |

These results demonstrate that the majority of positions of the CDR3 domains of the D2E7 VL region and VH region are amenable to substitution with a single alanine residue. Substitution of a single alanine at position 1, 4, 5, or 7 of the D2E7 VL CDR3 domain or at position 2, 5, 6, 8, 9 or 10 of the D2E7 VH CDR3 domain does not significantly affect the off rate of hTNFα binding as compared to the wild-type parental D2E7 antibody. Substitution of alanine at position 8 of the D2E7 VL CDR3 or at position 3 of the D2E7 VH CDR3 gives a 4-fold faster $K_{off}$ and an alanine substitution at position 4 or 11 of D2E7 VH CDR3 gives an 8-fold faster $K_{off}$, indicating that these positions are more critical for binding to hTNFα. However, a single alanine substitution at position 1, 4, 5, 7 or 8 of the D2E7 VL CDR3 domain or at position 2, 3, 4, 5, 6, 8, 9, 10 or 11 of the D2E7 VH CDR3 domain still results in an anti-hTNFα antibody having a $K_{off}$ of 1×10$^{-3}$ sec$^{-1}$ or less.

EXAMPLE 3

Binding Analysis of D2E7-Related Antibodies

A series of antibodies related in sequence to D2E7 were analyzed for their binding to rhTNFα, as compared to D2E7, by surface plasmon resonance as described in Example 1. The amino acid sequences of the VL regions tested are shown in FIGS. 1A and 1B. The amino acid sequences of the VH regions tested are shown in FIGS. 2A and 2B. The $K_{off}$ rates for various VH/VL pairs (in the indicated format, either as a full-length IgG1 or IgG4 antibody or as a scFv) are summarized below in Table 3:

TABLE 3

Binding of D2E7-Related Antibodies to Biotinylated rhTNFα

| VH | VL | Format | $K_{off}$ (sec$^{-1}$) |
|---|---|---|---|
| D2E7 VH | D2E7 VL | IgG1/IgG4 | 9.65 × 10$^{-5}$ |
| VH1-D2 | LOE7 | IgG1/IgG4 | 7.7 × 10$^{-5}$ |
| VH1-D2 | LOE7 | scFv | 4.6 × 10$^{-4}$ |

TABLE 3-continued

Binding of D2E7-Related Antibodies to Biotinylated rhTNFα

| VH | VL | Format | $K_{off}$ (sec$^{-1}$) |
|---|---|---|---|
| VH1-D2.N | LOE7.T | IgG4 | $2.1 \times 10^{-5}$ |
| VH1-D2.Y | LOE7.A | IgG4 | $2.7 \times 10^{-5}$ |
| VH1-D2.N | LOE7.A | IgG4 | $3.2 \times 10^{-5}$ |
| VH1-D2 | EP B12 | scFv | $8.0 \times 10^{-4}$ |
| VH1-D2 | 2SD4 VL | scFv | $1.94 \times 10^{-3}$ |
| 3C-H2 | LOE7 | scFv | $1.5 \times 10^{-3}$ |
| 2SD4 VH | LOE7 | scFv | $6.07 \times 10^{-3}$ |
| 2SD4 VH | 2SD4 VL | scFv | $1.37 \times 10^{-2}$ |
| VH1A11 | 2SD4 VL | scFv | $1.34 \times 10^{-2}$ |
| VH1B12 | 2SD4 VL | scFv | $1.01 \times 10^{-2}$ |
| VH1B11 | 2SD4 VL | scFv | $9.8 \times 10^{-3}$ |
| VH1E4 | 2SD4 VL | scFv | $1.59 \times 10^{-2}$ |
| VH1F6 | 2SD4 VL | scFv | $2.29 \times 10^{-2}$ |
| VH1D8 | 2SD4 VL | scFv | $9.5 \times 10^{-3}$ |
| VH1G1 | 2SD4 VL | scFv | $2.14 \times 10^{-2}$ |
| 2SD4 VH | EP B12 | scFv | $6.7 \times 10^{-3}$ |
| 2SD4 VH | VL10E4 | scFv | $9.6 \times 10^{-3}$ |
| 2SD4 VH | VL100A9 | scFv | $1.33 \times 10^{-2}$ |
| 2SD4 VH | VL100D2 | scFv | $1.41 \times 10^{-2}$ |
| 2SD4 VH | VL10F4 | scFv | $1.11 \times 10^{-2}$ |
| 2SD4 VH | VLLOE5 | scFv | $1.16 \times 10^{-2}$ |
| 2SD4 VH | VLL0F9 | scFv | $6.09 \times 10^{-3}$ |
| 2SD4 VH | VLL0F10 | scFv | $1.34 \times 10^{-2}$ |
| 2SD4 VH | VLLOG7 | scFv | $1.56 \times 10^{-2}$ |
| 2SD4 VH | VLLOG9 | scFv | $1.46 \times 10^{-2}$ |
| 2SD4 VH | VLLOH1 | scFv | $1.17 \times 10^{-2}$ |
| 2SD4 VH | VLLOH10 | scFv | $1.12 \times 10^{-2}$ |
| 2SD4 VH | VL1B7 | scFv | $1.3 \times 10^{-2}$ |
| 2SD4 VH | VL1C1 | scFv | $1.36 \times 10^{-2}$ |
| 2SD4 VH | VL1C7 | scFv | $2.0 \times 10^{-2}$ |
| 2SD4 VH | VL0.1F4 | scFv | $1.76 \times 10^{-2}$ |
| 2SD4 VH | VL0.1H8 | scFv | $1.14 \times 10^{-2}$ |

The slow off rates (i.e., $K_{off} \leq 1 \times 10^{-4}$ sec$^{-1}$) for full-length antibodies (i.e., IgG format) having a VL selected from D2E7, LOE7, LOE7.T and LOE7.A, which have either a threonine or an alanine at position 9, indicate that position 9 of the D2E7 VL CDR3 can be occupied by either of these two residues without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Furthermore, the slow off rates (i.e., $K_{off} \leq 1 \times 10^{-4}$ sec$^{-1}$) for antibodies having a VH selected from D2E7, VH1-D2.N and VH1-D2.Y, which have either a tyrosine or an asparagine at position 12, indicate that position 12 of the D2E7 VH CDR3 can be occupied by either of these two residues without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4).

The results shown in Table 3 demonstrate that, in scFv format, antibodies containing the 2SD4 VL or VH CDR3 region exhibit a faster $K_{off}$ (i.e., $K_{off} \geq 1 \times 10^{-3}$ sec$^{-1}$) as compared to antibodies containing the D2E7 VL or VH CDR3 region. Within the VL CDR3, 2SD4 differs from D2E7 at positions 2, 5 and 9. As discussed above, however, position 9 may be occupied by Ala (as in 2SD4) or Thr (as in D2E7) without substantially affecting the $K_{off}$. Thus, by comparison of 2SD4 and D2E7, positions 2 and 5 of the D2E7 VL CDR3, both arginines, can be identified as being critical for the association of the antibody with hTNFα. These residues could be directly involved as contact residues in the antibody binding site or could contribute critically to maintaining the scaffolding architecture of the antibody molecule in this region. Regarding the importance of position 2, replacement of Arg (in LOE7, which has the same VL CDR3 as D2E7) with Lys (in EP B12) accelerates the off rate by a factor of two. Regarding the importance of position 5, replacement of Arg (in D2E7) with Ala (in LD2E7*.A5), as described in Example 2, also accelerates the off rate two-fold. Furthermore, without either Arg at positions 2 and 5 (in 2SD4), the off rate is five-fold faster. However, it should be noted that although position 5 is important for improved binding to hTNFα, a change at this position can be negated by changes at other positions, as seen in VLLOE4, VLLOH1 or VL0.1H8.

Within the VH CDR3, 2SD4 differs from D2E7 at positions 1, 7 and 12. As discussed above, however, position 12 may be occupied by Asn (as in 2SD4) or Tyr (as in D2E7) without substantially affecting the $K_{off}$. Thus, by comparison of 2SD4 and D2E7, positions 1 and 7 of the D2E7 VH CDR3 can be identified as being critical for binding to hTNFα. As discussed above, these residues could be directly involved as contact residues in the antibody binding site or could contribute critically to maintaining the scaffolding architecture of the antibody molecule in this region. Both positions are important for binding to hTNFα since when the 3C-H2 VH CDR3 (which has a valine to alanine change at position 1 with respect to the D2E7 VH CDR3) is used, the scFv has a 3-fold faster off rate than when the D2E7 VH CDR3 is used but this off rate is still four times slower than when the 2SD4 VH CDR3 is used (which has changes at both positions 1 and 7 with respect to the D2E7 VH CDR3).

EXAMPLE 4

Functional Activity of D2E7

To examine the functional activity of D2E7, the antibody was used in several assays that measure the ability of the antibody to inhibit hTNFα activity, either in vitro or in vivo.

A. Neutralization of TNFα-Induced Cytotoxicity in L929 Cells

Human recombinant TNFα (rhTNFα) causes cell cytotoxicity to murine L929 cells after an incubation period of 18–24 hours. Human anti-hTNFα antibodies were evaluated in L929 assays by coincubation of antibodies with rhTNFα and the cells as follows. A 96-well microtiter plate containing 100 µl of anti-hTNFα Abs was serially diluted ⅓ down the plate in duplicates using RPMI medium containing 10% fetal bovine serum (FBS). Fifty microliters of rhTNFα was added for a final concentration of 500 pg/ml in each sample well. The plates were then incubated for 30 minutes at room temperature. Next, 50 µl of TNFα-sensitive L929 mouse fibroblasts cells were added for a final concentration of $5 \times 10^4$ cells per well, including 1 µg/ml Actinomycin-D. Controls included medium plus cells and rhTNFα plus cells. These controls, and a TNFα standard curve, ranging from 2 ng/ml to 8.2 pg/ml, were used to determine the quality of the assay and provide a window of neutralization. The plates were then incubated overnight (18–24 hours) at 37° C. in 5% $CO_2$.

One hundred microliters of medium was removed from each well and 50 µl of 5 mg/ml 3,(4,4-dimethylthiazol-2-yl)2,5-diphenyl-tetrazolium bromide (MTT; commercially available from Sigma Chemical Co., St. Louis, Mo.) in PBS was added. The plates were then incubated for 4 hours at 37° C. Fifty microliters of 20% sodium dodecyl sulfate (SDS) was then added to each well and the plates were incubated overnight at 37° C. The optical density at 570/630 nm was measured, curves were plotted for each sample and $IC_{50}$s were determined by standard methods.

Representative results for human antibodies having various VL and VH pairs, as compared to the murine MAK 195 mAb, are shown in FIG. 3 and in Table 4 below.

TABLE 4

Neutralization of TNFα-Induced L929 Cytotoxicity

| VH | VL | Structure | IC$_{50}$, M |
|---|---|---|---|
| D2E7 | D2E7 | scFv | $1.1 \times 10^{-10}$ |
| D2E7 | D2E7 | IgG4 | $4.7 \times 10^{-11}$ |
| 2SD4 | 2SD4 | scFv/IgG1/IgG4 | $3.0 \times 10^{-7}$ |
| 2SD4 | LOE7 | scFv | $4.3 \times 10^{-8}$ |
| VH1-D2 | 2SD4 | scFv | $1.0 \times 10^{-8}$ |
| VH1-D2 | LOE7 | scFv/IgG1/IgG4 | $3.4 \times 10^{-10}$ |
| VH1-D2.Y | LOE7.T | IgG4 | $8.1 \times 10^{-11}$ |
| VH1-D2.N | LOE7.T | IgG4 | $1.3 \times 10^{-10}$ |
| VH1-D2.Y | LOE7.A | IgG4 | $2.8 \times 10^{-11}$ |
| VH1-D2.N | LOE7.A | IgG4 | $6.2 \times 10^{-11}$ |
| MAK 195 | MAK 195 | scFv | $1.9 \times 10^{-8}$ |
| MAK 195 | MAK195 | F(ab')$_2$ | $6.2 \times 10^{-11}$ |

The results in FIG. 3 and Table 4 demonstrate that the D2E7 human anti-hTNFα antibody, and various D2E7-related antibodies, neutralize TNFα-induced L929 cytotoxicity with a capacity approximately equivalent to that of the murine anti-hTNFα mAb MAK 195.

B. Inhibition of TNFα Binding to TNFα Receptors on U-937 Cells

The ability of human anti-hTNFα antibodies to inhibit the binding of hTNFα to hTNFα receptors on the surface of cells was examined using the U-937 cell line (ATCC No. CRL 1593), a human histiocytic cell line that expresses hTNFα receptors. U-937 cells were grown in RPMI 1640 medium supplemented with 10% fetal bovine serum (Hyclone A-1111, Hyclone Laboratories, Logan, Utah), L-glutamine (4 nM), HEPES buffer solution (10 mM), penicillin (100 µg/ml) and streptomycin (100 µg/ml). To examine the activity of full-length IgG antibodies, U-937 cells were preincubated with PBS supplemented with 1 mg/ml of human IgG (Sigma I-4506, Sigma Chemical Co., St. Louis, Mo.) for 45 minutes on ice and then cells were washed three times with binding buffer. For the receptor binding assay, U-937 cells (5×10$^6$ cells/well) were incubated in a binding buffer (PBS supplemented with 0.2% bovine serum albumin) in 96-well microtiter plates (Costar 3799, Costar Corp., Cambridge, Mass.) together with $^{125}$I-labeled rhTNFα (3×10$^{-10}$ M; 25 µCi/ml; obtained from NEN Research Products, Wilmington, Del.), with or without anti-hTNFα antibodies, in a total volume of 0.2 ml. The plates were incubated on ice for 1.5 hours. Then, 75 µl of each sample was transferred to 1.0 ml test tubes (Sarstedt 72.700, Sarstedt Corp., Princeton, N.J.) containing dibutylphthalate (Sigma D-2270, Sigma Chemical Co., St. Louis, Mo.) and dinonylphthalate (ICN 210733, ICN, Irvine, Calif.). The test tubes contained a 300 µl mixture of dibutylphthalate and dinonylphthalate, 2:1 volume ratio, respectively. Free (i.e., unbound) $^{125}$I-labeled rhTNFα was removed by microcentrifugation for five minutes. Then, each test tube end containing a cell pellet was cut with the aid of a microtube scissor (Bel-Art 210180001, Bel-Art Products, Pequannock, N.J.). The cell pellet contains $^{125}$I-labeled rhTNFα bound to the p60 or p80 TNFα receptor, whereas the aqueous phase above the oil mixture contains excess free $^{125}$I-labeled rhTNFα. All cell pellets were collected in a counting tube (Falcon 2052, Becton Dickinson Labware, Lincoln Park, N.J.) and counted in a scintillation counter.

Figure 4:
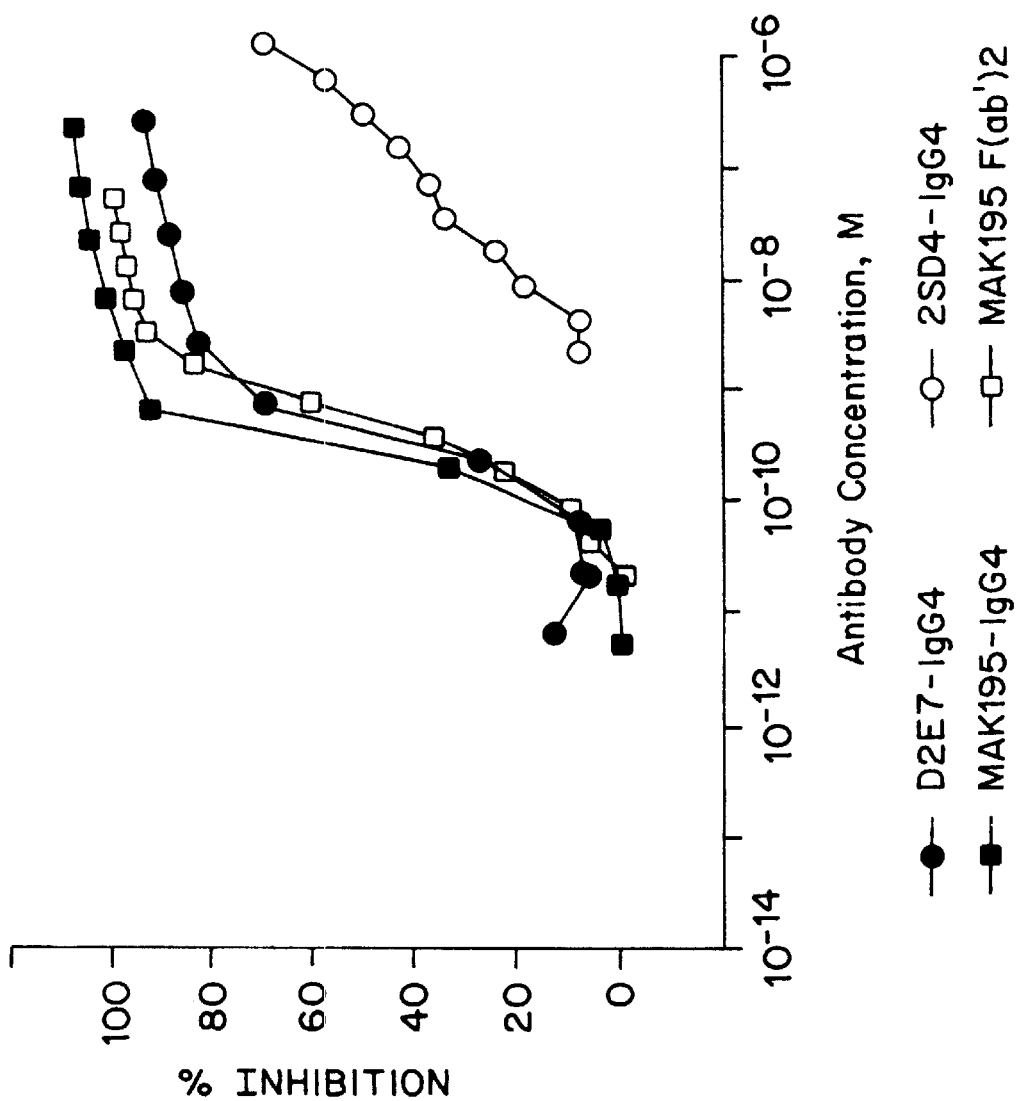
FIG. 4 is a graph depicting the inhibition of rhTNFα binding to hTNFα receptors on U-937 cells by the human anti-hTNFα antibody D2E7, as compared to the murine anti-hTNFα antibody MAK 195 (IgG1 or Fab fragment).

Representative results are shown in FIG. 4. The IC$_{50}$ value for D2E7 inhibition of hTNFα binding to hTNFα receptors on U-937 cells is approximately 3×10$^{-10}$ M. These results demonstrate that the D2E7 human anti-hTNFα antibody inhibits rhTNFα binding to hTNFα receptors on U-937 cells at concentrations approximately equivalent to that of the murine anti-hTNFα mAb MAK 195.

C. Inhibition of ELAM-1 Expression on HUVEC

Human umbilical vein endothelial cells (HUVEC) can be induced to express endothelial cell leukocyte adhesion molecule 1 (ELAM-1) on their cell-surface by treatment with rhTNFα, which can be detected by reacting rhTNFα-treated HUVEC with an mouse anti-human ELAM-1 antibody. The ability of human anti-hTNFα antibodies to inhibit this TNFα-induced expression of ELAM-1 on HUVEC was examined as follows: HUVEC (ATCC No. CRL 1730) were plated in 96-well plates (5×10$^4$ cells/well) and incubated overnight at 37 ° C. The following day, serial dilutions of human anti-hTNFα antibody (1:10) were prepared in a microtiter plate, starting with 20–100 µg/ml of antibody. A stock solution of rhTNFα was prepared at 4.5 ng/ml, aliquots of rhTNFα were added to each antibody-containing well and the contents were mixed well. Controls included medium alone, medium plus anti-hTNFα antibody and medium plus rhTNFα. The HUVEC plates were removed from their overnight incubation at 37° C. and the medium gently aspirated from each well. Two hundred microliters of the antibody-rhTNFα mixture were transferred to each well of the HUVEC plates. The HUVEC plates were then further incubated at 37° C. for 4 hours. Next, a murine anti-ELAM-1 antibody stock was diluted 1:1000 in RPMI. The medium in each well of the HUVEC plate was gently aspirated, 50 µl/well of the anti-ELAM-1 antibody solution was added and the HUVEC plates were incubated 60 minutes at room temperature. An $^{125}$I-labeled anti-mouse Ig antibody solution was prepared in RPMI (approximately 50,000 cpm in 50 µl). The medium in each well of the HUVEC plates was gently aspirated, the wells were washed twice with RPMI and 50 µl of the $^{125}$I-labeled anti-mouse Ig solution was added to each well. The plates were incubated for one hour at room temperature and then each well was washed three times with RPMI. One hundred eighty microliters of 5% SDS was added to each well to lyse the cells. The cell lysate from each well was then transferred to a tube and counted in a scintillation counter.

Figure 5:
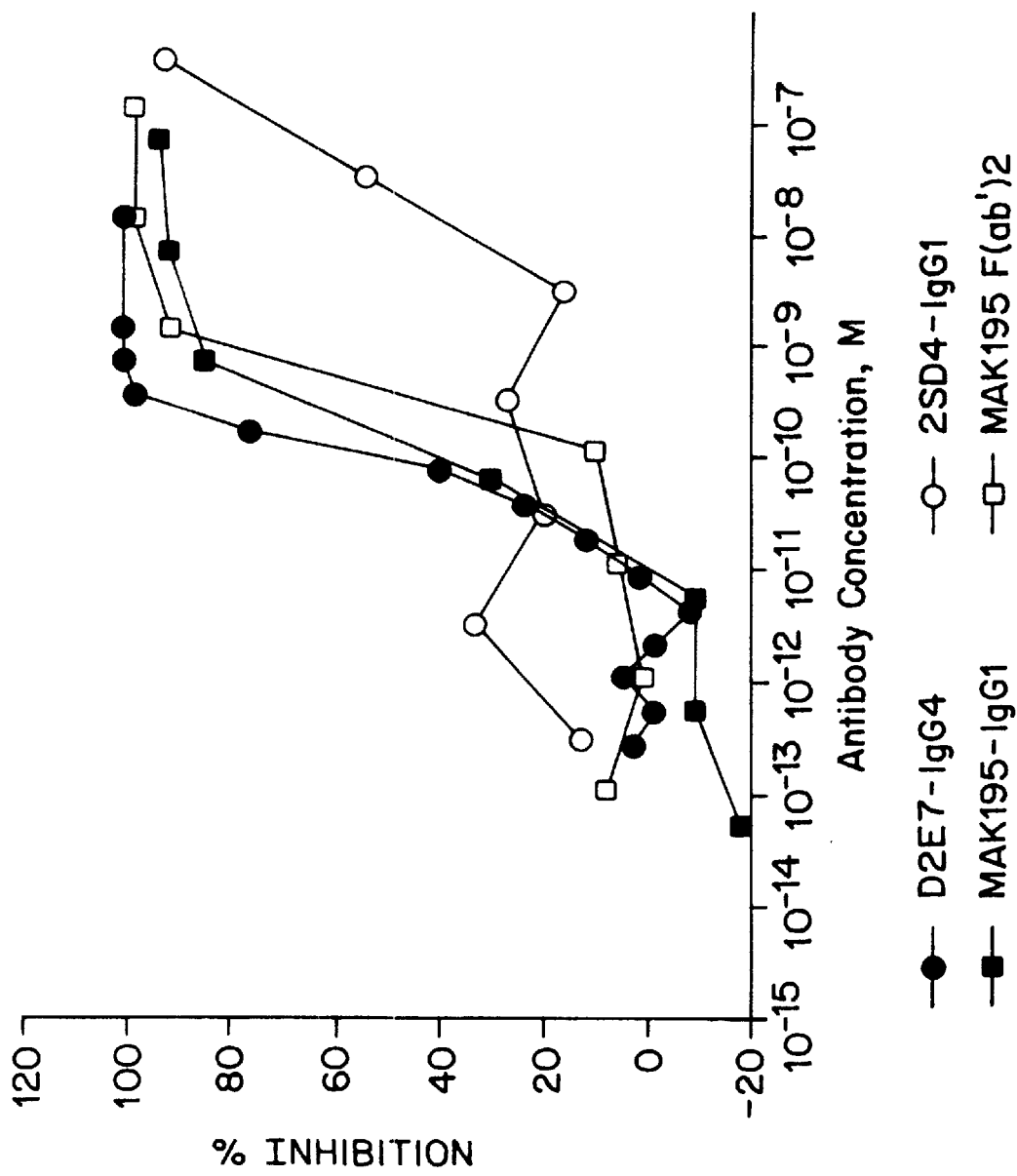
FIG. 5 is a graph depicting the inhibition of TNFα-induced ELAM-1 expression on HUVEC by the human anti-hTNFα antibody D2E7, as compared to the murine anti-hTNFα antibody MAK 195 (IgG1 or Fab fragment).

Representative results are shown in FIG. 5. The IC$_{50}$ value for D2E7 inhibition of hTNFα-induced expression of ELAM-1 on HUVEC is approximately 6×10$^{-11}$ M. These results demonstrate that the D2E7 human anti-hTNFα antibody inhibits the hTNFα-induced expression of ELAM-1 on HUVEC at concentrations approximately equivalent to that of the murine anti-hTNFα mAb MAK 195.

D. In Vivo Neutralization of hTNFα

Injection of recombinant human TNFα (rhTNFα) to D-galactosamine sensitized mice causes lethality within a 24 hour time period. TNFα neutralizing agents have been shown to prevent lethality in this model. To examine the ability of human anti-hTNFα antibodies to neutralize hTNFα in vivo in this model, C57B1/6 mice were injected with varying concentrations of D2E7-IgG1, or a control protein, in PBS intraperitoneally (i.p.). Mice were challenged 30 minutes later with 1 µg of rhTNFα and 20 mg of D-galactosamine in PBS i.p., and observed 24 hours later. These amount of rhTNFα and D-galactosamine were previously determined to achieve 80–90% lethality in these mice.

Figure 6:
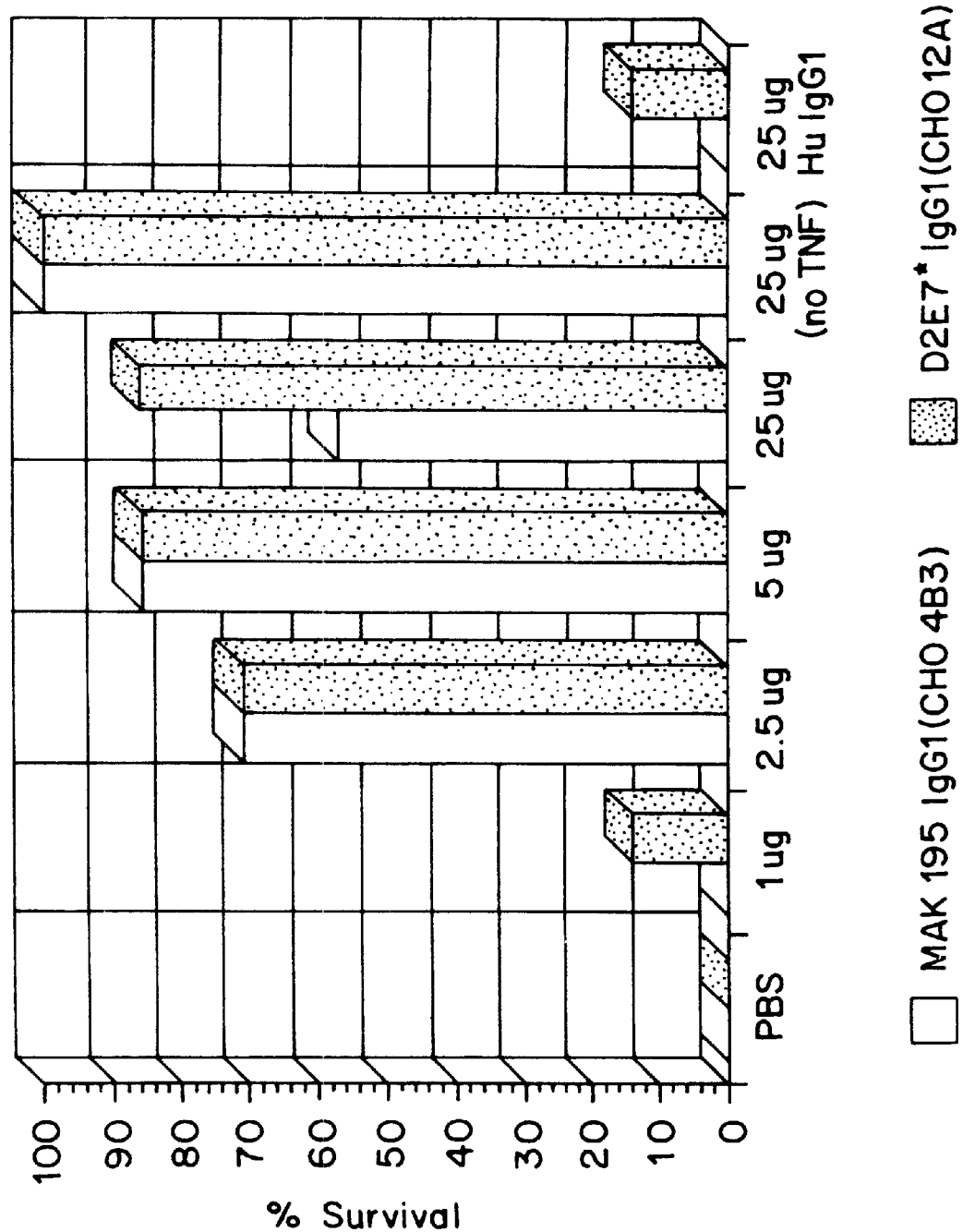
FIG. 6 is a bar graph depicting protection from TNFα-induced lethality in D-galactosamine-sensitized mice by administration of the human anti-hTNFα antibody D2E7 (black bars), as compared to the murine anti-hTNFα antibody MAK 195 (hatched bars).

Representative results, depicted as a bar graph of % survival versus antibody concentration, are shown in FIG. 6. The black bars represent D2E7, whereas the hatched bars represent MAK 195. Injection of 2.5–25 µg of D2E7 antibody per mouse protected the animals from TNFα-induced lethality. The $ED_{50}$ value is approximately 1–2.5 µg/mouse. The positive control antibody, MAK 195, was similar in its protective ability. Injection of D2E7 in the absence of rhTNFα did not have any detrimental effect on the mice. Injection of a non-specific human IgG1 antibody did not offer any protection from TNFα-induced lethality.

Additionally, in a hTNFα-mediated rabbit pyrexia model, D2E7 antibody attenuated the temperature rise due to administration of hTNFα in a dose dependent manner.

These results demonstrate that D2E7 is effective at inhibiting hTNFα activity in vivo.

E. D2E7 Neutralization of TNFαs from Other Species

The binding specificity of D2E7 was examined by measuring its ability to neutralize tumor necrosis factors from various primate species and from mouse, using an L929 cytotoxicity assay (as described in Example 4, subsection A, above). The results are summarized in Table 5 below:

TABLE 5

D2E7 Neutralization of TNFα from Different Species

| TNFα* | $IC_{50}$ for D2E7 Neutralization (M)** |
| --- | --- |
| Human | $6.0 \times 10^{-11}$ |
| Chimpanzee | $5.5 \times 10^{-11}$ |
| baboon | $6.0 \times 10^{-11}$ |
| marmoset | $4.0 \times 10^{-11}$ |
| cynomolgus | $8.0 \times 10^{-11}$ |
| rhesus | $\sim 3 \times 10^{-11}$ |
| mouse | $6.0 \times 10^{-8}$ |

The results in Table 5 demonstrate that D2E7 can neutralize the activity of five primate TNFαs approximately equivalently to human TNFα and, moreover, can neutralize the activity of mouse TNFα, albeit ~1000-fold less well than human TNFα. However, the $IC_{50}$ for neutralization of mouse TNFα ($6.0 \times 10^{-8}$ M) is still significant, as it compares to that of a hamster anti-mouse TNFα antibody commercially available (Genzyme Corp.) for detecting or inhibiting mouse TNFα. Moreover, D2E7 was found to bind to porcine TNFα but did not specifically bind to other cytokines, such as lymphotoxin (TNFβ), IL-1α, IL-1β, IL-2, IL-4, IL-6, IL-8, IFNγ and TGFβ.

Forming part of the present disclosure is the appended Sequence Listing, the contents of which are summarized in the table below:

| SEQ ID NO: | ANTIBODY CHAIN | REGION | SEQUENCE TYPE |
| --- | --- | --- | --- |
| 1 | D2E7 | VL | amino acid |
| 2 | D2E7 | VH | amino acid |
| 3 | D2E7 | VL CDR3 | amino acid |
| 4 | D2E7 | VH CDR3 | amino acid |
| 5 | D2E7 | VL CDR2 | amino acid |
| 6 | D2E7 | VH CDR2 | amino acid |
| 7 | D2E7 | VL CDR1 | amino acid |
| 8 | D2E7 | VH CDR1 | amino acid |
| 9 | 2SD4 | VL | amino acid |
| 10 | 2SD4 | VH | amino acid |
| 11 | 2SD4 | VL CDR3 | amino acid |
| 12 | EP B12 | VL CDR3 | amino acid |
| 13 | VL10E4 | VL CDR3 | amino acid |
| 14 | VL100A9 | VL CDR3 | amino acid |
| 15 | VLL100D2 | VL CDR3 | amino acid |
| 16 | VLL0F4 | VL CDR3 | amino acid |
| 17 | LOE5 | VL CDR3 | amino acid |
| 18 | VLLOG7 | VL CDR3 | amino acid |
| 19 | VLLOG9 | VL CDR3 | amino acid |
| 20 | VLLOH1 | VL CDR3 | amino acid |
| 21 | VLLOH10 | VL CDR3 | amino acid |
| 22 | VL1B7 | VL CDR3 | amino acid |
| 23 | VL1C1 | VL CDR3 | amino acid |
| 24 | VL0.1F4 | VL CDR3 | amino acid |
| 25 | VL0.1H8 | VL CDR3 | amino acid |
| 26 | LOE7.A | VL CDR3 | amino acid |
| 27 | 2SD4 | VH CDR3 | amino acid |
| 28 | VH1B11 | VH CDR3 | amino acid |
| 29 | VH1D8 | VH CDR3 | amino acid |
| 30 | VH1A11 | VH CDR3 | amino acid |
| 31 | VH1B12 | VH CDR3 | amino acid |
| 32 | VH1E4 | VH CDR3 | amino acid |
| 33 | VH1F6 | VH CDR3 | amino acid |
| 34 | 3C-H2 | VH CDR3 | amino acid |
| 35 | VH1-D2.N | VH CDR3 | amino acid |
| 36 | D2E7 | VL | nucleic acid |
| 37 | D2E7 | VH | nucleic acid |

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 107 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

(2) INFORMATION FOR SEQ ID NO:2:

(i) SEQUENCE CHARACTERISTICS:
        (A) LENGTH: 121 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:2:

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is Thr or Ala"

(xi) SEQUENCE DESCRIPTION: SEQ ID NO:3:

```
Gln Arg Tyr Asn Arg Ala Pro Tyr Xaa
1               5
```

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 12
        (D) OTHER INFORMATION: /note= "Xaa is Tyr or Asn"

(xi) SEQUENCE DESCRIPTION: SEQ ID NO:4:

```
Val Ser Tyr Leu Ser Thr Ala Ser Ser Leu Asp Xaa
1               5                   10
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Ala Ala Ser Thr Leu Gln Ser
1               5
```

(2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Ala Ile Thr Trp Asn Ser Gly His Ile Asp Tyr Ala Asp Ser Val Glu
1               5                   10                  15
Gly
```

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

```
Arg Ala Ser Gln Gly Ile Arg Asn Tyr Leu Ala
1               5                   10
```

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

```
Asp Tyr Ala Met His
1               5
```

(2) INFORMATION FOR SEQ ID NO:9:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

```
Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
                100                 105
```

(2) INFORMATION FOR SEQ ID NO:10:

(i) SEQUENCE CHARACTERISTICS:
        (A) LENGTH: 121 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
```

```
             65                  70                  75                  80
Leu Gln Met Asn Ser Leu Arg Pro Glu Asp Thr Ala Val Tyr Tyr Cys
                         85                  90                  95
Thr Lys Ala Ser Tyr Leu Ser Thr Ser Ser Leu Asp Asn Trp Gly
                 100                 105                 110
Gln Gly Thr Leu Val Thr Val Ser Ser
             115                 120
```

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

```
Gln Lys Tyr Asn Ser Ala Pro Tyr Ala
1               5
```

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Gln Lys Tyr Asn Arg Ala Pro Tyr Ala
1               5
```

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Gln Lys Tyr Gln Arg Ala Pro Tyr Thr
1               5
```

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

```
Gln Lys Tyr Ser Ser Ala Pro Tyr Thr
1               5
```

(2) INFORMATION FOR SEQ ID NO:15:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

Gln Lys Tyr Asn Ser Ala Pro Tyr Thr
1           5

(2) INFORMATION FOR SEQ ID NO:16:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

Gln Lys Tyr Asn Arg Ala Pro Tyr Thr
1           5

(2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

Gln Lys Tyr Asn Ser Ala Pro Tyr Tyr
1           5

(2) INFORMATION FOR SEQ ID NO:18:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

Gln Lys Tyr Asn Ser Ala Pro Tyr Asn
1           5

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

Gln Lys Tyr Thr Ser Ala Pro Tyr Thr
1               5

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

Gln Lys Tyr Asn Arg Ala Pro Tyr Asn
1               5

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:21:

Gln Lys Tyr Asn Ser Ala Ala Tyr Ser
1               5

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

Gln Gln Tyr Asn Ser Ala Pro Asp Thr
1               5

(2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

Gln Lys Tyr Asn Ser Asp Pro Tyr Thr
1               5

(2) INFORMATION FOR SEQ ID NO:24:

(i) SEQUENCE CHARACTERISTICS:
        (A) LENGTH: 9 amino acids

```
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Gln Lys Tyr Ile Ser Ala Pro Tyr Thr
 1               5

(2) INFORMATION FOR SEQ ID NO:25:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:25:

Gln Lys Tyr Asn Arg Pro Pro Tyr Thr
 1               5

(2) INFORMATION FOR SEQ ID NO:26:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:26:

Gln Arg Tyr Asn Arg Ala Pro Tyr Ala
 1               5

(2) INFORMATION FOR SEQ ID NO:27:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:27:

Ala Ser Tyr Leu Ser Thr Ser Ser Ser Leu Asp Asn
 1               5                  10

(2) INFORMATION FOR SEQ ID NO:28:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:28:

Ala Ser Tyr Leu Ser Thr Ser Ser Ser Leu Asp Lys
 1               5                  10
```

(2) INFORMATION FOR SEQ ID NO:29:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

Ala Ser Tyr Leu Ser Thr Ser Ser Ser Leu Asp Tyr
1               5                   10

(2) INFORMATION FOR SEQ ID NO:30:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

Ala Ser Tyr Leu Ser Thr Ser Ser Ser Leu Asp Asp
1               5                   10

(2) INFORMATION FOR SEQ ID NO:31:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

Ala Ser Tyr Leu Ser Thr Ser Phe Ser Leu Asp Tyr
1               5                   10

(2) INFORMATION FOR SEQ ID NO:32:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

Ala Ser Tyr Leu Ser Thr Ser Ser Ser Leu His Tyr
1               5                   10

(2) INFORMATION FOR SEQ ID NO:33:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

Ala Ser Phe Leu Ser Thr Ser Ser Ser Leu Glu Tyr
1               5                   10

(2) INFORMATION FOR SEQ ID NO:34:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

Ala Ser Tyr Leu Ser Thr Ala Ser Ser Leu Glu Tyr
1               5                   10

(2) INFORMATION FOR SEQ ID NO:35:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

Val Ser Tyr Leu Ser Thr Ala Ser Ser Leu Asp Asn
1               5                   10

(2) INFORMATION FOR SEQ ID NO:36:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:36:

| | | | | | |
|---|---|---|---|---|---|
| GACATCCAGA | TGACCCAGTC | TCCATCCTCC | CTGTCTGCAT | CTGTAGGGGA | CAGAGTCACC | 60 |
| ATCACTTGTC | GGGCAAGTCA | GGGCATCAGA | AATTACTTAG | CCTGGTATCA | GCAAAAACCA | 120 |
| GGGAAAGCCC | CTAAGCTCCT | GATCTATGCT | GCATCCACTT | TGCAATCAGG | GGTCCCATCT | 180 |
| CGGTTCAGTG | GCAGTGGATC | TGGGACAGAT | TTCACTCTCA | CCATCAGCAG | CCTACAGCCT | 240 |
| GAAGATGTTG | CAACTTATTA | CTGTCAAAGG | TATAACCGTG | CACCGTATAC | TTTTGGCCAG | 300 |
| GGGACCAAGG | TGGAAATCAA | A | | | | 321 |

(2) INFORMATION FOR SEQ ID NO:37:

(i) SEQUENCE CHARACTERISTICS:
        (A) LENGTH: 363 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:37:

-continued

| | | | | | |
|---|---|---|---|---|---|
| GAGGTGCAGC | TGGTGGAGTC | TGGGGGAGGC | TTGGTACAGC | CCGGCAGGTC | CCTGAGACTC | 60 |
| TCCTGTGCGG | CCTCTGGATT | CACCTTTGAT | GATTATGCCA | TGCACTGGGT | CCGGCAAGCT | 120 |
| CCAGGGAAGG | GCCTGGAATG | GGTCTCAGCT | ATCACTTGGA | ATAGTGGTCA | CATAGACTAT | 180 |
| GCGGACTCTG | TGGAGGGCCG | ATTCACCATC | TCCAGAGACA | ACGCCAAGAA | CTCCCTGTAT | 240 |
| CTGCAAATGA | ACAGTCTGAG | AGCTGAGGAT | ACGGCCGTAT | ATTACTGTGC | GAAAGTCTCG | 300 |
| TACCTTAGCA | CCGCGTCCTC | CCTTGACTAT | TGGGGCCAAG | GTACCCTGGT | CACCGTCTCG | 360 |
| AGT | | | | | | 363 |

What is claimed is:

1. A method for inhibiting human TNFα activity comprising contacting human TNFα with an antibody such that human TNFα activity is inhibited, wherein the antibody is an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

2. A method for inhibiting human TNFα activity comprising contacting human TNFα with an antibody such that human TNFα activity is inhibited, wherein the antibody is an isolated human antibody, or antigen-binding portion thereof, with the following characteristics:
   a) dissociates from human TNFα with a $K_{off}$ rate constant of $1 \times 10^{-3}$ s$^{-1}$ or less, as determined by surface plasmon resonance;
   b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;
   c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

3. A method for inhibiting human TNFα activity comprising contacting human TNFα with an antibody such that human TNFα activity is inhibited, wherein the antibody is an isolated human antibody, or an antigen binding portion thereof, with a light chain variable region (LCVR) comprising the amino acid sequence of SEQ ID NO: 1 and a heavy chain variable region (HCVR) comprising The amino acid sequence of SEQ ID NO: 2.

4. A method for inhibiting human TNFα activity in a human subject suffering from a disorder in which TNFα activity is detrimental, comprising administering to the human subject an antibody such that human TNFα activity in the human subject is inhibited, wherein the antibody is an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

5. A method for inhibiting human TNFα activity in a human subject suffering from a disorder in which TNFα activity is detrimental, comprising administering to the human subject an antibody such that human TNFα activity in the human subject is inhibited, wherein the antibody is an isolated human antibody, or antigen-binding portion thereof, with the following characteristics:
   a) dissociates from human TNFα with a $K_{off}$ rate constant of $1 \times 10^{-3}$ s$^{-1}$ or less, as determined by surface plasmon resonance;
   b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;
   c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

6. A method for inhibiting human TNFα activity in a human subject suffering from a disorder in which TNFα activity is detrimental, comprising administering to the human subject an antibody such that human TNFα activity in the human subject is inhibited, wherein The antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2.

7. A method for inhibiting human TNFα activity in a human subject suffering from a disorder in which TNFα activity is detrimental, comprising administering to the human subject an antibody such that human TNFα activity in the human subject is inhibited, wherein the antibody is D2E7.

8. The method of any one of claims 4, 5, 6, and 7 wherein the disorder is an autoimmune disease.

9. The method of any one of claims 4, 5, 6, and 7 wherein the disorder is an infectious disease.

10. The method of any one of claims 4, 5, 6, and 7 wherein the disorder is transplant rejection or graft-versus-host disease.

11. The method of any one of claims 4, 5, 6, and 7 wherein the disorder is a malignancy.

12. The method of any one of claims 4, 5, 6, and 7 wherein the disorder is a pulmonary disorder.

13. The method of any one of and claims 4, 5, 6, and 7 wherein the disorder is an intestinal disorder.

14. The method of any one of claims 4, 5, 6, and 7 wherein the disorder is a cardiac disorder.

15. The method of any one of claim 4, 5, 6, and 7 wherein the disorder is sepsis.

16. The method of claim 15, wherein the antibody is administered to the human subject together with the cytokine interleukin-6 (IL-6) or is administered to a human subject with a serum or plasma concentration of IL-6 above 500 pg/ml.

17. The method of any one of claims 4, 5, 6, and 7 wherein the disorder is rheumatoid arthritis.

18. The method of any one of claims 4, 5, 6, and 7 wherein the disorder is rheumatoid spondylitis.

19. The method of any one of claims 4, 5, 6, and 7 wherein the disorder is osteoarthritis.

20. The method any one of claims 4, 5, 6, and 7 wherein the disorder is gouty arthritis.

21. The method of any one of claims 4, 5, 6, and 7 wherein the disorder is an allergy.

22. The method of any one of claims 4, 5, 6, and 7 wherein the disorder is multiple sclerosis.

23. The method of any one of claims 4, 5, 6, and 7 wherein the disorder is autoimmune diabetes.

24. The method of any one of claims 4, 5, 6, and 7 wherein the disorder is autoimmune uveitis.

25. The method of any one of claims 4, 5, 6, and 7 wherein the disorder is nephrotic syndrome.

26. The method of any one of claims 4, 5, 6, and 7 wherein the disorder is inflammatory bone disorders.

27. The method of any one of claims 4, 5, 6, and 7 wherein the disorder is bone resorption disease.

28. The method of any one of claims 4, 5, 6, and 7 wherein the disorder is alcoholic hepatitis.

29. The method of any one of claims 4, 5, 6, and 7 wherein the disorder is viral hepatitis.

30. The method of any one of claims 4, 5, 6, and 7 wherein the disorder is coagulation disturbances.

31. The method of any one of claims 4, 5, 6, and 7 wherein the disorder is burns.

32. The method of any one of claims 4, 5, 6, and 7 wherein the disorder is reperfusion injury.

33. The method of any one of claims 4, 5, 6, and 7 wherein the disorder is keloid formation.

34. The method of claim any one of claims 4, 5, 6, and 7 wherein the disorder is scar tissue formation.

35. The method of any one of claims 4, 5, 6, and 7 wherein the disorder is pyrexia.

36. A method for treating a subject suffering from a disorder in which TNFα activity is detrimental, comprising administering to the subject an antibody such that the disorder is treated, wherein the antibody is an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

37. A method for treating a subject suffering from a disorder in which TNFα activity is detrimental, comprising administering to the subject an antibody such that the disorder is treated, wherein the antibody is an isolated human antibody, or antigen-binding portion thereof, with the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

38. A method for treating a subject suffering from a disorder in which TNFα activity is detrimental, comprising administering to the subject an antibody such that the disorder is treated, wherein the antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2.

39. A method for treating a subject suffering from a disorder in which TNFα activity is detrimental, comprising administering to the subject an antibody such that the disorder is treated, wherein the antibody is D2E7.

40. The method of any one of claims 36, 37, 38, and 39 wherein the disorder is an autoimmune disease.

41. The method of any one of claims 36, 37, 38, and 39 wherein the disorder is an infectious disease.

42. The method of any one of claims 36, 37, 38, and 39 wherein the disorder is transplant rejection or graft-versus-host disease.

43. The method of any one of claims 36, 37, 38, and 39 wherein the disorder is a malignancy.

44. The method of any one of claims 36, 37, 38, and 39 wherein the disorder is a pulmonary disorder.

45. The method of any one of claims 36, 37, 38, and 39 wherein the disorder is an intestinal disorder.

46. The method of any one of claims 36, 37, 38, and 39 wherein the disorder is a cardiac disorder.

47. The method of any one of claims 36, 37, 38, and 39 wherein the disorder is sepsis.

48. The method of claim 47, wherein the antibody is administered to a human subject together with the cytokine interleukin-6 (IL-6) or is administered to a human subject with a serum or plasma concentration of IL-6 above 500 pg/ml.

49. The method of any one of claims 36, 37, 38, and 39 wherein the disorder is rheumatoid arthritis.

50. The method of any one of claims 36, 37, 38, and 39 wherein the disorder is rheumatoid spondylitis.

51. The method of any one of claims 36, 37, 38, and 39 wherein the disorder is osteoarthritis.

52. The method any one of claims 36, 37, 38, and 39 wherein the disorder is gouty arthritis.

53. The method of any one of claims 36, 37, 38, and 39 wherein the disorder is an allergy.

54. The method of any one of claims 36, 37, 38, and 39 wherein the disorder is multiple sclerosis.

55. The method of any one of claims 36, 37, 38, and 39 wherein the disorder is autoimmune diabetes.

56. The method of any one of claims 36, 37, 38, and 39 wherein the disorder is autoimmune uveitis.

57. The method of any one of claims 36, 37, 38, and 39 wherein the disorder is nephrotic syndrome.

58. The method of any one of claims 36, 37, 38, and 39 wherein the disorder is inflammatory bone disorders.

59. The method of any one of claims 36, 37, 38, and 39 wherein the disorder is bone resorption disease.

60. The method of any one of claims 36, 37, 38, and 39 wherein the disorder is alcoholic hepatitis.

61. The method of any one of claims 36, 37, 38, and 39 wherein the disorder is viral hepatitis.

62. The method of any one of claims 36, 37, 38, and 39 wherein the disorder is coagulation disturbances.

63. The method of any one of claims 36, 37, 38, and 39 wherein the disorder is burns.

64. The method of any one of claims 36, 37, 38, and 39 wherein the disorder is reperfusion injury.

65. The method of any one of claims 36, 37, 38, and 39 wherein the disorder is keloid formation.

66. The method of claim any one of claims 36, 37, 38, and 39 wherein the disorder is scar tissue formation.

67. The method of any one of claims 36, 37, 38, and 39 wherein the disorder is pyrexia.

68. The method of any one of claims 4, 5, 6, 7, 36, 37, 38, and 39 wherein the isolated human antibody is combined with a pharmaceutically acceptable carrier.

69. The method of claim 4, 5, 6, 7, 36, 37, 38, and 39 wherein the isolated human antibody is administered with at least one additional therapeutic agent.

70. The method of any one of claims 36, 37, 38, and 39 wherein the subject is human.

71. The method of any one of claims 36, 37, 38, and 39 wherein the disorder is septic shock.

72. The method of any one of claims 36, 37, 38, and 39 wherein the disorder is endotoxic shock.

73. The method of any one of claims 36, 37, 38, and 39 wherein the disorder is gram negative sepsis.

74. The method of any one of claims 36, 37, 38, and 39 wherein the disorder is toxic shock syndrome.

75. The method of any one of claims 36, 37, 38, and 39 wherein the disorder is malaria.

76. The method of any one of claims 36, 37, 38, and 39 wherein the disorder is meningitis.

77. The method of any one of claims 36, 37, 38, and 39 wherein the disorder is cachexia.

78. The method of any one of claims 36, 37, 38, and 39 wherein the disorder is AIDS.

79. The method of any one of claims 36, 37, 38, and 39 wherein the disorder is bacterical meningitis.

80. The method of any one of claims 36, 37, 38, and 39 wherein the disorder is AIDS-related complex (ARC).

81. The method of any one of claims 36, 37, 38, and 39 wherein the disorder is cytomegalovirus infection secondary to transplantation.

82. The method of any one of claims 36, 37, 38, and 39 wherein the disorder is fever and myalgias due to infection.

83. The method of any one of claims 36, 37, 38, and 39 wherein the disorder is allograft rejection.

84. The method of any one of claims 36, 37, 38, and 39 wherein the disorder is stimulating tumor growth.

85. The method of any one of claims 36, 37, 38, and 39 wherein the disorder is enhancing metastatic potential and mediating cytotoxicity in malignancies.

86. The method of any one of claims 36, 37, 38, and 39 wherein the disorder is inhibiting tumor growth or metastasis.

87. The method of any one of claims 36, 37, 38, and 39 wherein the disorder is adult respiratory distress syndrome.

88. The method of any one of claims 36, 37, 38, and 39 wherein the disorder is shock lung.

89. The method of any one of claims 36, 37, 38, and 39 wherein the disorder is chronic pulmonary inflammatory disease.

90. The method of any one of claims 36, 37, 38, and 39 wherein the disorder is pulmonary sarcoidosis.

91. The method of any one of claims 36, 37, 38, and 39 wherein the disorder is pulmonary fibrosis.

92. The method of any one of claims 36, 37, 38, and 39 wherein the disorder is silicosis.

93. The method of any one of claims 36, 37, 38, and 39 wherein the disorder is inflammatory bowel disorder.

94. The method of any one of claims 36, 37, 38, and 39 wherein the disorder is idiopathic inflammatory bowel disease.

95. The method of any one of claims 36, 37, 38, and 39 wherein the disorder is Crohn's disease.

96. The method of any one of claims 36, 37, 38, and 39 wherein the disorder is ulcerative colitis.

97. The method of any one of claims 36, 37, 38, and 39 wherein the disorder is ischemia of the heart.

98. The method of any one of claims 36, 37, 38, and 39 wherein the disorder is heart insufficiency.

99. The method of any one of claims 36, 37, 38, and 39 wherein the disorder is hepatitis.

100. The method of any one of claims 36, 37, 38, and 39 wherein the cachexia secondary to infection.

\* \* \* \* \*